US012605260B2

(12) United States Patent
Anderson et al.

(10) Patent No.: US 12,605,260 B2
(45) Date of Patent: Apr. 21, 2026

(54) PROSTHETIC FOOT WITH REINFORCED SPRING CONNECTION

(71) Applicant: OTTO BOCK HEALTHCARE LP, Minneapolis, MN (US)

(72) Inventors: Vaughn Roy Anderson, Highland, UT (US); Brandon Anderson, West Jordan, UT (US)

(73) Assignee: OTTO BOCK HEALTHCARE LP, Austin, TX (US)

( * ) Notice: Subject to any disclaimer, the term of this patent is extended or adjusted under 35 U.S.C. 154(b) by 388 days.

(21) Appl. No.: 16/212,359

(22) Filed: Dec. 6, 2018

(65) Prior Publication Data

US 2020/0179138 A1 Jun. 11, 2020

(51) Int. Cl.
*A61F 2/66* (2006.01)
*A61F 2/50* (2006.01)

(52) U.S. Cl.
CPC ........ *A61F 2/66* (2013.01); *A61F 2002/5001* (2013.01); *A61F 2002/5007* (2013.01); *A61F 2002/5056* (2013.01); *A61F 2002/5093* (2013.01); *A61F 2002/6642* (2013.01); *A61F 2002/665* (2013.01); *A61F 2002/6664* (2013.01); *A61F 2002/6678* (2013.01)

(58) Field of Classification Search
CPC .. A61F 2/60; A61F 2/66; A61F 2/6607; A61F 2002/6621–6635
See application file for complete search history.

(56) References Cited

U.S. PATENT DOCUMENTS 456,206 A * 7/1891 Rowley ..................... A61F 2/66
623/55
6,811,571 B1 11/2004 Phillips
(Continued)

FOREIGN PATENT DOCUMENTS

CN 106456339 A 2/2017
GB 2265089 A 9/1993

OTHER PUBLICATIONS

"International Search Report and Written Opinion of the International Searching Authority," issued in connection with Int'l Appl. No. PCT/US2019/064709, dated Feb. 26, 2020 (9 pages).
(Continued)

*Primary Examiner* — Marcia L Watkins
(74) *Attorney, Agent, or Firm* — HOLLAND & HART LLP

(57) ABSTRACT

A prosthetic foot having a base spring having a toe end portion and a heel end portion, and a top spring assembly. The top spring assembly includes a first spring member having a distal end and a proximal end, a second spring member spaced apart from the first spring member along substantially an entire length of the first spring member, the second spring member having a distal end and a proximal end, a first bond connection provided between the distal ends of the first and second spring members, a second bond connection provided between the distal end of the second spring member and a top surface of the base spring in a forefoot portion of the base spring, and a spring connector extending through at least a first hole formed in the base spring, the second bond connection and the second spring member.

22 Claims, 17 Drawing Sheets

(56)                    References Cited

U.S. PATENT DOCUMENTS

| | | | |
|---|---|---|---|
| 9,808,358 B2 | 11/2017 | Mosler et al. | |
| 2009/0012630 A1* | 1/2009 | Mosler | A61F 2/66 |
| | | | 623/55 |
| 2010/0042228 A1 | 2/2010 | Doddroe et al. | |
| 2011/0320012 A1* | 12/2011 | Christensen | A61F 2/66 |
| | | | 623/55 |
| 2012/0179274 A1* | 7/2012 | Christensen | A61F 2/66 |
| | | | 623/55 |
| 2014/0039642 A1* | 2/2014 | Nijiman | A61F 2/66 |
| | | | 623/33 |
| 2014/0046456 A1* | 2/2014 | Smith | A61F 2/66 |
| | | | 623/55 |
| 2015/0289996 A1* | 10/2015 | Smith | A61F 2/66 |
| | | | 623/53 |
| 2015/0328020 A1 | 11/2015 | Clausen et al. | |
| 2016/0081821 A1 | 3/2016 | Sandahl | |
| 2016/0143750 A1 | 5/2016 | Kranner et al. | |
| 2017/0049584 A1 | 2/2017 | Pusch et al. | |
| 2018/0296370 A1 | 10/2018 | Jonsson et al. | |

OTHER PUBLICATIONS

Chinese Patent Application No. 201980091462.X; First Office Action
dated Dec. 9, 2023; 23 pages.

* cited by examiner

900

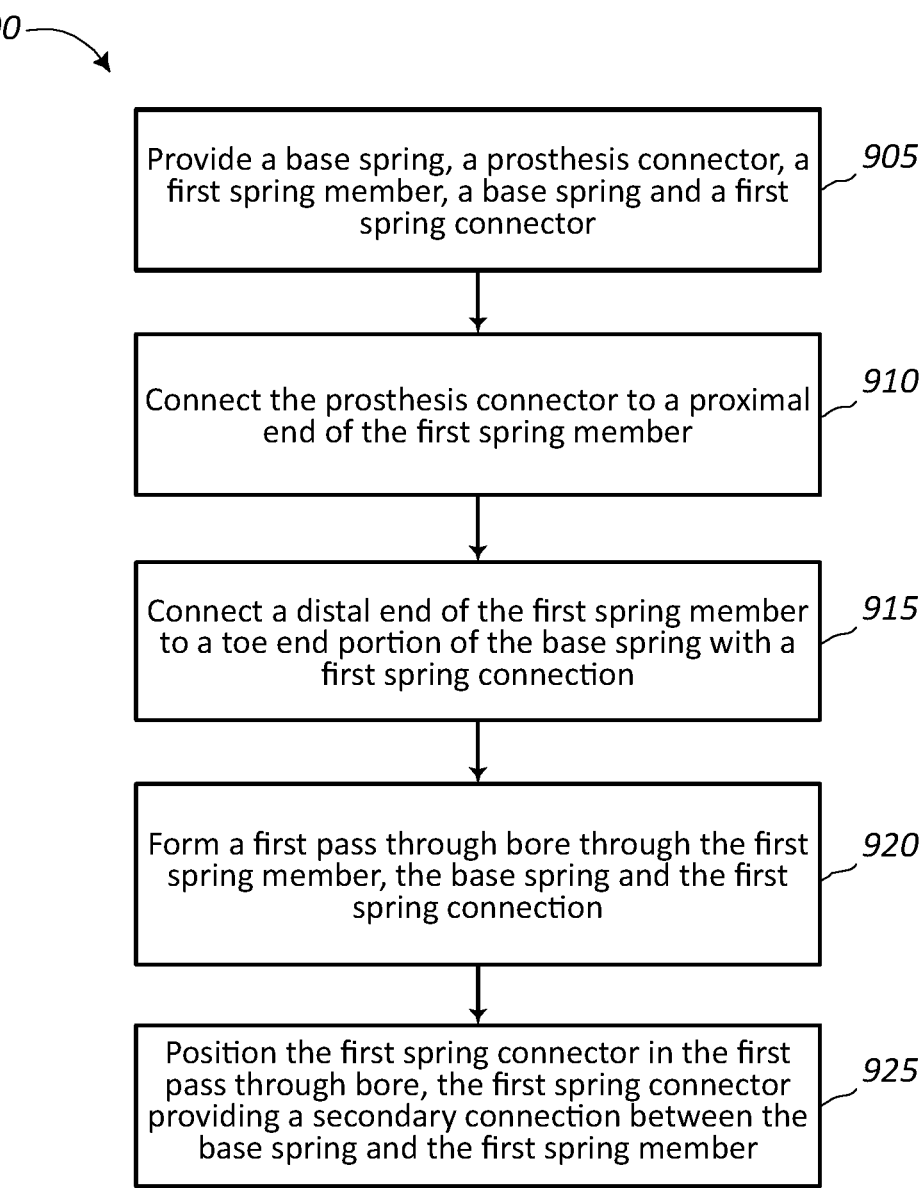

Provide a base spring, a prosthesis connector, a first spring member, a base spring and a first spring connector    905

Connect the prosthesis connector to a proximal end of the first spring member    910

Connect a distal end of the first spring member to a toe end portion of the base spring with a first spring connection    915

Form a first pass through bore through the first spring member, the base spring and the first spring connection    920

Position the first spring connector in the first pass through bore, the first spring connector providing a secondary connection between the base spring and the first spring member    925

*FIG. 22*

PROSTHETIC FOOT WITH REINFORCED SPRING CONNECTION

TECHNICAL FIELD

The present disclosure relates generally to prosthetic devices, and more particularly relates to prosthetic feet having improved connections between spring members of the feet.

BACKGROUND

Prosthetic feet serve as distal termination for a prosthetic device and can be fixed to a below knee tube, which is fastened to a prosthetic knee joint, directly to a prosthetic shank or to the prosthetic knee joint. To this end, connection features are regularly provided at the proximal end on the prosthetic foot in order to establish a stable and permanent connection with the proximal prosthetic component. Prosthetic feet are usually provided with a cosmetic covering, which consist of plastic and are embodied approximately in the form of a natural foot.

From the structural point of view, the simplest form of a prosthetic foot is a rigid foot. However, a rigid foot has significant disadvantages in view of the elastic properties or the rollover properties. More complex designs include dampening elements or heel springs for damping the momentum upon heel strike. It is likewise possible for a spring to be arranged in the forefoot region in order to enhance the rollover characteristics of the foot during the stance phase and to store and then release deformation energy so as to assist the prosthetic foot user when walking.

Many prosthetic foot designs have attempted to copy the anatomy of the foot or simulate its actions by replacing the bones and muscle with various mechanical components. Other designs have departed radically from mere anatomical copying or mechanical simulation by replacing the entire foot with an energy storage element such as a spring. As the user steps onto the foot, the user's weight compresses or bends one or more springs. As the user moves forward, the user's weight comes off the foot and the energy stored in the spring is used to propel the user forward. In order to achieve the necessary strength and flexibility of the prosthetic foot, multiple spring members or varying thicknesses are used. The type of connection between the spring members may influence the stiffness and characteristics of the foot. A flexible joint between spring elements may be desirable because it allows for slight relative movement between spring elements, which may advantageously alter the stiffness of the device or the stress distribution in one or more spring elements. Depending on the foot and joint design, the joint movement may be sliding and/or rotational, which results in shear stresses, tension and compression stresses, or a combination of these stresses in the flexible joint. Due to these movements and stresses, a flexible joint can be subject to fatigue failure. Preventing a bond failure of this nature may be a primary objective for many prosthetic foot designs in order to prevent the heel/foot plate member from becoming detached from the resilient forefoot members.

In order to prevent a failure at the connection between the foot springs, manufacturers of prosthetics will typically bolt the foot springs together, as taught in U.S. Patent Publication Nos. 2005/0038525a1, 2018/0014949A1, and 2012/0271434 and U.S. Pat. Nos. 6,942,704 and 5,181,933. Some products have used bulky straps to limit joint movement and provide a failsafe feature as taught in U.S. Pat. No. 3,098, 239. Other products are bonded over a large area as taught in U.S. Pat. No. 7,347,877. This large bond area decreases movement within a joint and essentially eliminates many of the advantages of a flexible joint, particularly when using foot springs comprising carbon material.

Another option for securing the foot springs together includes wrapping an exterior of the foot springs with a resin impregnated fiber as taught in U.S. Pat. No. 6,241,776. Wrapping with resin impregnated fiber results in a rigid connection, similar to a bolted connection.

In all of these options, most benefits of any flexible bond in place between the foot springs (e.g., soft rollover, enhanced standing stability, enhanced medial/lateral movement, and a lighter weight foot) are effectively eliminated. Carbon fiber has one of the highest strength/weight ratios of all materials available, hence it is both lightweight and durable. However, carbon fiber materials are also very stiff and the strength is directional. Hence, constructing a foot that is both highly durable and functional (i.e., flexible) from carbon fiber composite material is a considerable design challenge. A flexible joint increases the flexibility of the foot. Therefore, opportunities exist for improvements in prosthetic feet designs.

SUMMARY

One aspect of the present disclosure relates to a prosthetic foot having a base spring having a toe end portion and a heel end portion, and a top spring assembly. The base spring and the spring members of the top spring assembly may have an elongate, plate-like shape, which may be curved along an axis and linear in a width direction. The top spring assembly includes a first spring member having a distal or anterior end and a proximal or posterior end, a second spring member spaced apart from the first spring member along substantially an entire length of the first spring member, the second spring member having a distal or anterior end and a proximal or posterior end, and a first bond connection provided between the distal or anterior ends of the first and second spring members. The prosthetic foot may also include a second bond connection provided between the distal or anterior end of the second spring member and a top surface of the base spring in a forefoot portion of the base spring, and a spring connector extending through at least a first hole formed in the base spring, the second bond connection and the second spring member.

The first hole may also be formed in the first bond connection and the first spring member. The spring connector may have a generally cylindrical cross section, may include multiple fibers or filaments, and may be considered a collection of threads. The spring connector may include one or more of a thread, a string, a strand, a cord, a tow, a roving, a braid, a lashing, and a cable. The spring connector is preferably stiff in the longitudinal or axial direction, but flexible in transverse directions that allows the spring connector to bend around corners easily and be tied into a knot. Such a configuration also allows for some shearing movement between spring members. The fibrous nature of the spring connector also provides ample fiber surface area for adhesion as the ends of the spring connector may be fixed by, for example, an adhesive or other bonding agent. The spring connector may include a polymer material selected from the group comprising at least polyester, nylon, Kevlar®, Dyneema® and Spectra®, or may comprise metal fibers or other materials. The prosthetic foot may further include a second hole, the second hole being formed in the base spring, the second bond connection and the second spring member, and the spring connector may have a loop shaped construction that passes through the first and second holes. The prosthetic foot may also include a secondary spring connector and third and fourth holes, the third and fourth holes being formed in the base spring, the second bond connection and the second spring member, and the second-ary spring connector may have a loop shaped construction that passes through the third and fourth holes. The prosthetic foot may include a spacer positioned between the proximal ends of the first and second spring members. The first bond connection may provide a spacing between the distal ends of the first and second spring members. The first and second bond connections may be provided by an adhesive. The prosthetic foot may include a heel cushion mounted to the base spring at a location spaced forward of a heel end of the base spring, and the heel cushion may be arranged to contact a bottom surface of the second spring member during use of the prosthetic foot. The ends of the spring connector may be secured with, for example, a knot, an adhesive, melting, or a combination of these.

Another aspect of the present disclosure relates to a prosthetic foot that includes a prosthesis connector config-ured to connect the prosthetic foot to a lower limb prosthe-sis, a base spring having a toe end portion and a heel end portion, a first spring member having a distal end and a proximal end, a first bond connection provided between the distal end of the first spring member and a top surface of the base spring, and a spring connector positioned in a first pass through bore. The first pass through bore extends through at least the base spring and the first spring member. In some embodiments, the first pass through bore may additionally extend through the first spring connection.

The spring connector may have a loop shaped construc-tion. The spring connector may include one or more of a thread, a string, a cord, a tow, a roving, a braid, and a cable. The spring connector may include a flexible material selected from the group consisting of polyester, nylon, Kevlar®, Dyneema® and Spectra®. The prosthetic foot may include a second pass through bore, the second pass through bore extending through the base spring, the first bond connection and the first spring member, and the spring connector passes through the first and second pass through bores. The prosthetic foot may include a secondary spring connector and third and fourth holes, the third and fourth holes being formed in the base spring and the second spring member, and the secondary spring connector has a loop shaped construction that passes through the third and fourth holes. In some embodiments, the third and fourth holes may additionally extend through the second bond connection. The first bond connection may include an elastomeric mate-rial. The prosthetic foot may further include a second spring member arranged generally parallel with and spaced apart from the first spring member, the second spring member having a distal end and a proximal end, and a second bond connection provided between the distal ends of the first and second spring members, wherein the first pass through bore extends through the second bond connection and the second spring member.

A further aspect of the present disclosure relates to a method of manufacturing a prosthetic foot. The method includes providing a base spring, a prosthesis connector, a first spring member, base spring and a first spring connector, connecting the prosthesis connector to a proximal end of the first spring member, connecting a distal end of the first spring member to a toe end portion of the base spring with a first spring connection, forming a first pass through bore through the first spring member, the base spring and the first spring connection, and positioning the first spring connector in the first pass through bore, the first spring connector providing a secondary connection between the base spring and the first spring member.

The method may include forming a second pass through bore through the first spring member, the base spring and the first spring connection, and positioning the first spring connector in the second pass through bore, the first spring connector having a loop shape. The method may include providing a second spring member and arranging the second spring member in parallel with and spaced apart from the first spring member, and connecting distal ends of the first and second spring members to each other with a second spring connection, wherein the first pass through bore extends through the second spring member and the second spring connection, and the first spring connector provides at least one of a secondary connection between the first and second spring members and a connection between the sec-ond spring member and the base spring. The method may include forming third and fourth pass through bores through the first spring member, the base spring and the first spring connection, and positioning a second spring connector in the third and fourth pass through bores, the second spring connector providing another secondary connection between the base spring and the first spring member. The method may include forming a second pass through bore through the first spring member, the base spring and the first spring connec-tion, and positioning a second spring connector in the second pass through bore, the second spring connector providing another secondary connection between the base spring and the first spring member. The method may also include forming a second pass through bore through the first and second spring members, the base spring, and the first and second spring connections, and positioning the first spring connector in the second pass through bore, the second spring connector having a loop shape.

A further aspect of the present disclosure relates to a prosthetic device for use external to the human body. The prosthetic device includes a first elongate, plate-like mem-ber, a second elongate, plate-like member, at least two holes extending through each of the first and second elongate, plate-like members, and a cord looped through the at least two holes to secure the first and second elongate, plate-like members together.

The cord may include opposite positioned free ends, and the free ends of the cord may be at least partially secured together with a knot. The cord may include opposite posi-tioned free ends, and the free ends of the cord are at least partially secured together with an adhesive. The first and second elongate, plate-like members may be secured to each other with a bond connection, and the cord passes through the bond connection.

The foregoing has outlined rather broadly the features and technical advantages of examples according to the disclo-sure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the spirit and scope of the appended claims. Features which are believed to be char-acteristic of the concepts disclosed herein, both as to their organization and method of operation, together with asso-ciated advantages will be better understood from the fol-lowing description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the embodiments may be realized by reference to the following drawings. In the appended figures, similar components or features may have the same reference label.

FIG. 22 is a flow diagram illustrating steps of an example method in accordance with the present disclosure.

Figure 1:
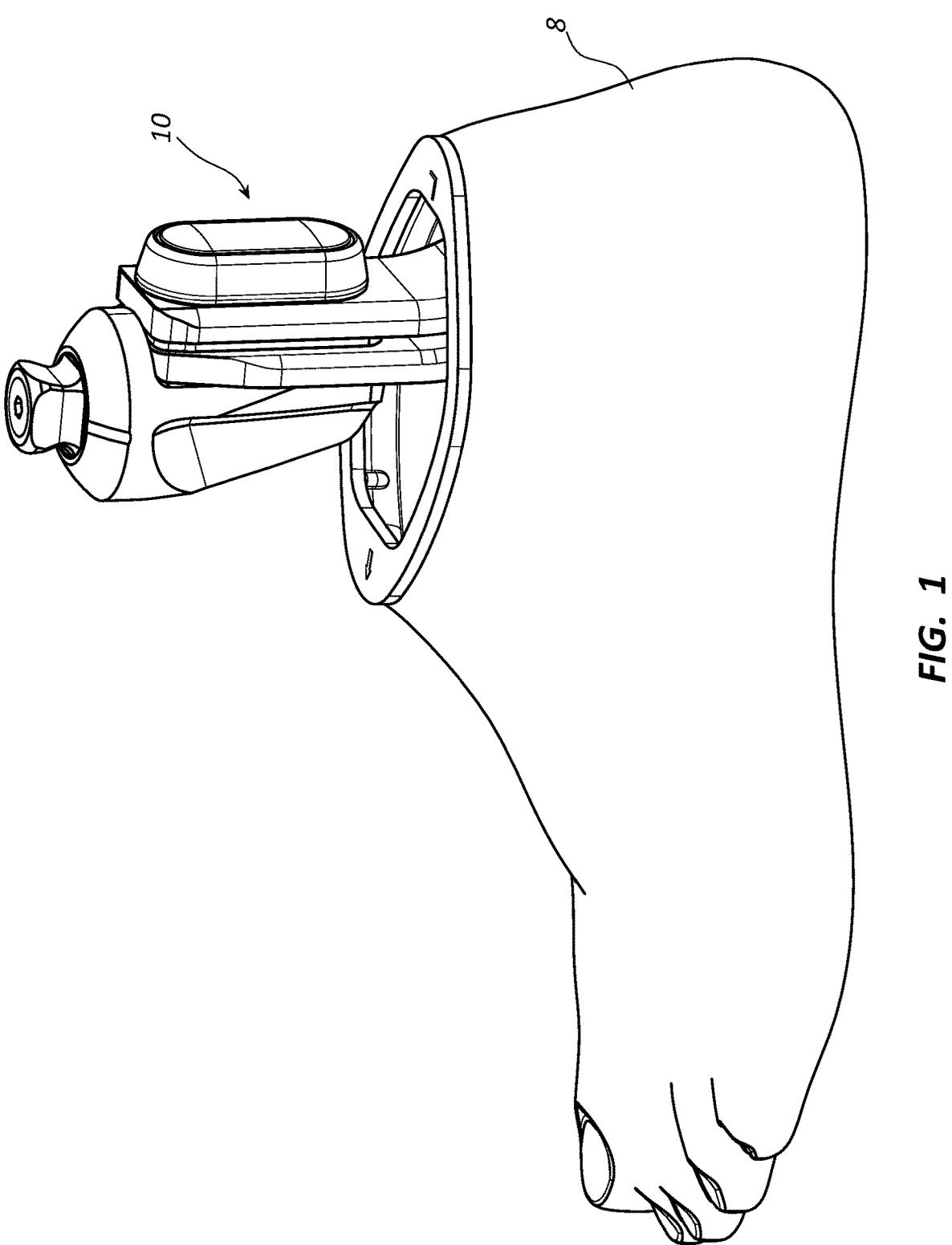
FIG. 1 is a side perspective view of an example prosthetic foot assembly in accordance with the present disclosure.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The present disclosure is generally directed to prosthetic devices, and more particularly relates to prosthetic foot devices, which are also referred to as a foot prostheses. The prosthetic foot embodiments disclosed herein may provide certain advantages as compared to other prosthetic foot devices.

The present disclosure relates to a resilient prosthetic foot that has a reinforcement to a flexible bond between at least one spring component of the prosthetic foot and a second component of the prosthetic foot. More particularly, the present disclosure relates to a prosthetic foot having at least a resilient forefoot member (also referred to as top springs, spring members, or elongate, plate-like members or springs) and at least one resilient distal heel/foot plate member (also referred to as a base spring or elongate, plate-like member or spring) and the connection there between. The flexible bond between foot spring members is reinforced using a separate connection member in the form of, for example, a thread, a string, a strand, a cord, a tow, a roving, a braid, a lashing or a cable that is fed through the flexible bond and foot spring members, much like sewing a button onto clothing. The connection member may be inextensible, meaning that the connection member does not change length, but is still flexible to change shape. The connection member provides a connection between the foot spring members that maintains flexibility and functionality of the spring members while not substantially changing the stiffness of the foot.

The present disclosure also relates to a resilient prosthetic foot having a plurality of resilient top spring members and at least one base spring. The resilient top spring members are rigidly connected together at their proximal ends and connected to the base spring at their distal ends via a flexible bond. The flexible bond between the top spring members and the base spring is reinforced with a separate connector that extends through one or more holes formed in the base spring and at least one of the top springs. The holes may be referred to as apertures or pass through bores, and may be pre-formed. The connector may include a resistant thread, string, or cord that that comprises a material such as polyester, nylon, Kevlar®, Dyneema®, or Spectra®. The connector may be a straight, elongate structure that extends through a single hole or pass through bore, or may be a loop-shaped structure that extends through multiple holes or pass through bores. The connector may be position in, for example, the forefoot are of the prosthetic foot.

Another aspect of the present disclosure relates to a prosthetic foot with improved connection between the base spring and the one or more top springs. In at least some examples, the improved connection may have an increased fatigue life in the range of 2-6 times greater than if a resilient bond connection alone is used. The present disclosure may provide a safer failure condition related to the bond connection. In the unlikely event of a bond failure, the foot remains assembled due to the additional connector, thus reducing the risk of injury to the user.

The present disclosure provides for a flexible connection between the heel/foot plate member (also referred to as a base spring) and the resilient forefoot member(s) (also referred to as top springs), which results from a stitched connection (e.g., using a fiber, cord, cable, or the like) verses a more rigid connection (e.g., bolt, rod, screw, or the like), to better maintain desired spring characteristics and performance of the prosthetic foot.

The present disclosure may also provide for a shorter bond (in a longitudinal direction along a length of the prosthetic foot) between the heel/foot plate member and the resilient forefoot member(s), which may enhance spring characteristics of the prosthetic foot. This shorter bond length may also increase an effective length of the foot spring(s).

The present disclosure may also allow for a more consistent bond to be achieved between the heel/foot plate member and the resilient forefoot member(s) during manufacturing (i.e., the manufacturing process could include stitching to include x-number of loops or stitches).

Referring now to FIGS. 1-8, an example prosthetic foot assembly is shown including a prosthetic foot 10 and a foot casing 8. The foot casing 8 is a host structure in which portions of the prosthetic foot are positioned. The foot casing 8 provides an aesthetic covering for the prosthetic foot 10 to give the appearance of an actual foot. The foot casing 8 is shown in FIG. 1, with the remaining FIGS. 2-8 being focused on the prosthetic foot 10. The prosthetic foot 10 is intended to be used inside a shoe, and the prosthetic foot 10 with foot casing 8 may be inserted together into a shoe.

Referring to FIGS. 2-8, the prosthetic foot 10 is shown including a basis spring 12, first top spring 14, a second top spring 16, a prosthesis connector 18, first and second bond connections 20, 22, and first and second spring connectors 24a, 24b (also referred to as stitching, strand, cable and the like). The first top spring 14 is connected to the base spring 12 in a toe end area of the prosthetic foot 10 using the first bond connection 20. The first bond connection 20 may be formed using, for example, an adhesive bond.

The first top spring 14 and base spring 12 may be further connected together using the first and second spring connectors 24a, 24b. The first and second spring connectors 24a, 24b may extend through the base spring 12, the first top spring 14, and the first bond connection 20. Sets of preformed holes 26a, 28a and 26b, 28b may be formed in the base spring 12, first top spring 14 and first bond connection 20 to define a path through which the first and second spring connectors 24a, 24b may extend to provide a positive connection between the base spring 12 and first top spring 14. The pre-formed holes 26, 28 may be referred to as passthrough bores, apertures, or the like. The spring connectors 24a, 24b may provide a secondary connection in addition to the primary connection provided by the bond connection 20. The spring connectors 24a, 24b may preferably be stiff in the longitudinal or axial direction, but flexible in transverse directions that allows the spring connectors 24a, 24b to bend around corners easily and/or be tied into a knot. The ends of the spring connectors 24a, 24b may be secured to each other, for example, with a knot, adhesive, by melting, or a combination of these.

The first and second bond connections 20, 22 may be formed using an elastic, flexible material that provides at least some relative movement between the base spring 12 and first and second top springs 14, 16 (e.g., rotation movement about a transverse, longitudinal, and/or vertical axis, compression, and/or translational movement in the anterior/posterior and/or medial/lateral direction). The second bond connection 22 may provide the sole connection point between the first and second top springs 14, 16. In some embodiments, as described below, at least one of the first and second spring connectors 24a, 24b may extend through the second top spring 16 and second bond connection 22 to provide a positive connection between the base spring 12 and the first and second top springs 14, 16.

Typically, the use of at least one of the first and second spring connectors 24a, 24b in addition to the first bond connection 20 significantly reduces the probability of the first bond connection 20 failing during use of the prosthetic foot 10. Failure of the first bond connection 20 typically would result in disconnection of the base spring 12 from the first top spring 14. Furthermore, use of at least one of the first and second spring connectors 24a, 24b may also reduce the required length of the first bond connection 20 along the length dimension of the prosthetic foot 10. The length of the first bond connection 20 (as described below) may impact the spring characteristics of the base spring 12 and/or the first and second top springs 14, 16, and therefore the performance of the foot.

The prosthesis connector 18 may be releasably attached to the first and second top springs 14, 16 at their proximal ends. In at least one example, the prosthesis connector 18 is releasably attached using one or more fasteners 32a, 32b. Prosthesis connectors with different connector features such as a pyramid connector may be used. In at least some examples, the pyramid connector is a replaceable component of the prosthesis connector 18. In other embodiments, the pyramid connector is integrally formed with remaining portions of the prosthesis connector 18, and mounted directly to one or both of the first and second top springs 14, 16. Other connector features besides a pyramid connector maybe used as part of the prosthesis connector 18 for securing the prosthetic foot 10 to another prosthetic member such as a lower leg pylon, a socket, or the like.

The prosthetic foot 10 may also include a heel cushion 34 and a heel cushion seat 36. Typically, the heel cushion 34 is mounted directly to a top surface of a basis spring 12 and arranged to contact a bottom surface of the first top spring 14 as shown in, for example, FIG. 6. The heel cushion 34 may be releasably connected to the base spring 12. Alternatively, heel cushion 34 may be releasably connected to the first top spring 14. In at least some examples, the heel cushion 34 is connected to the base spring 12 with an interference fit connection using, for example, the heel cushion seat 36, which is mounted to the top surface of the base spring 12. The heel cushion 34 may be replaceable with heel cushions having different properties, such as increased or reduced stiffness, compressibility, damping capability, etc. Heel cushions of different sizes and shapes may also be used in place of the heel cushion 34 shown in the figures. The heel cushion may include, for example, surface texture or a pattern of surface features on surfaces that contact other components of the prosthetic foot to reduce or eliminate "suction cup", clapping, or other undesirable noises when the prosthetic foot is in use. In some examples, the prosthetic foot 10 may be operable without any heel cushion 34 and/or associated heel cushion seat 36.

Figure 2:
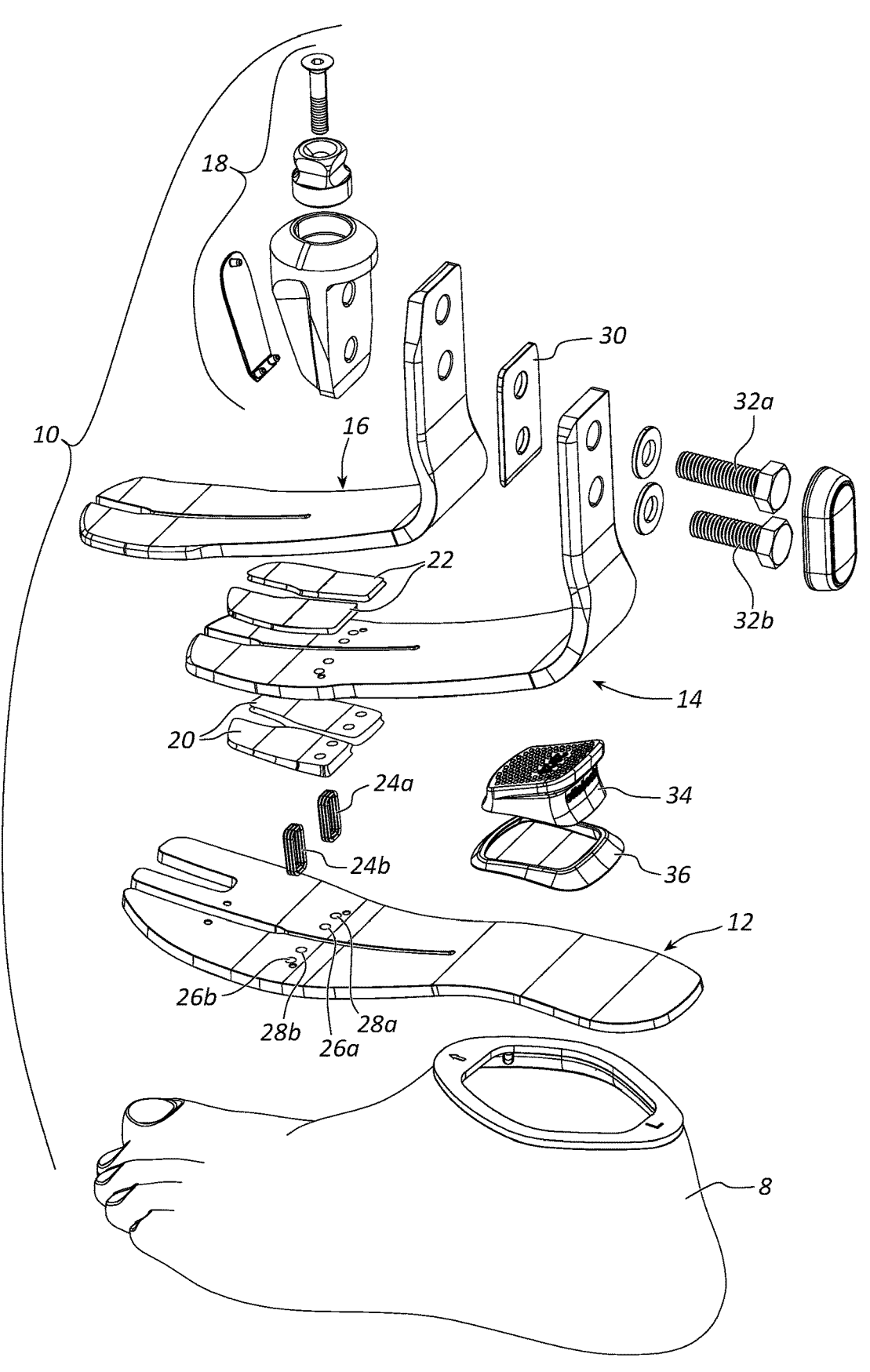
FIG. 2 is an exploded perspective view of the prosthetic foot assembly shown in FIG. 1.
Figure 3:
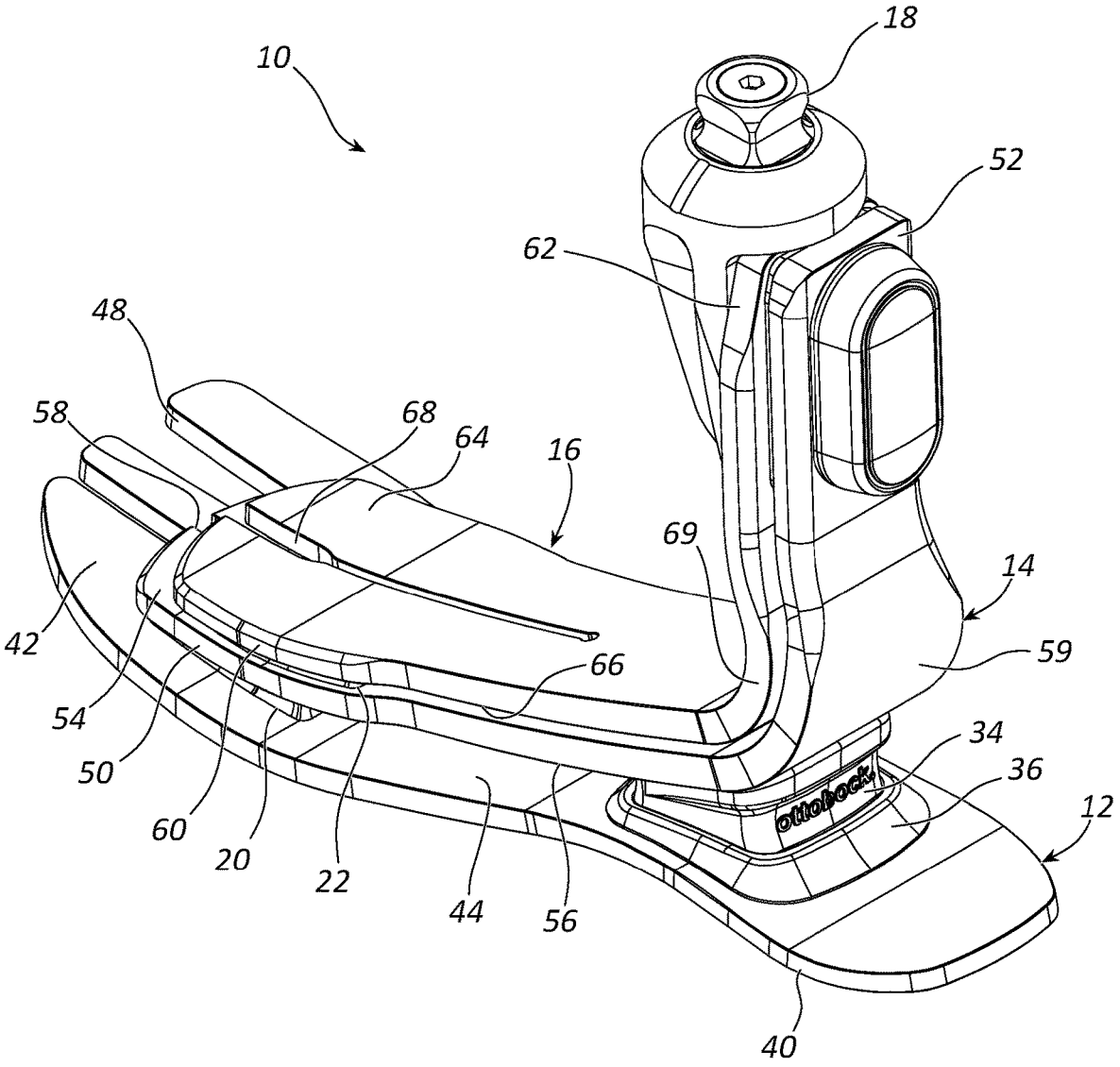
FIG. 3 is a rear perspective view of a prosthetic foot shown in FIG. 1.
Figure 4:
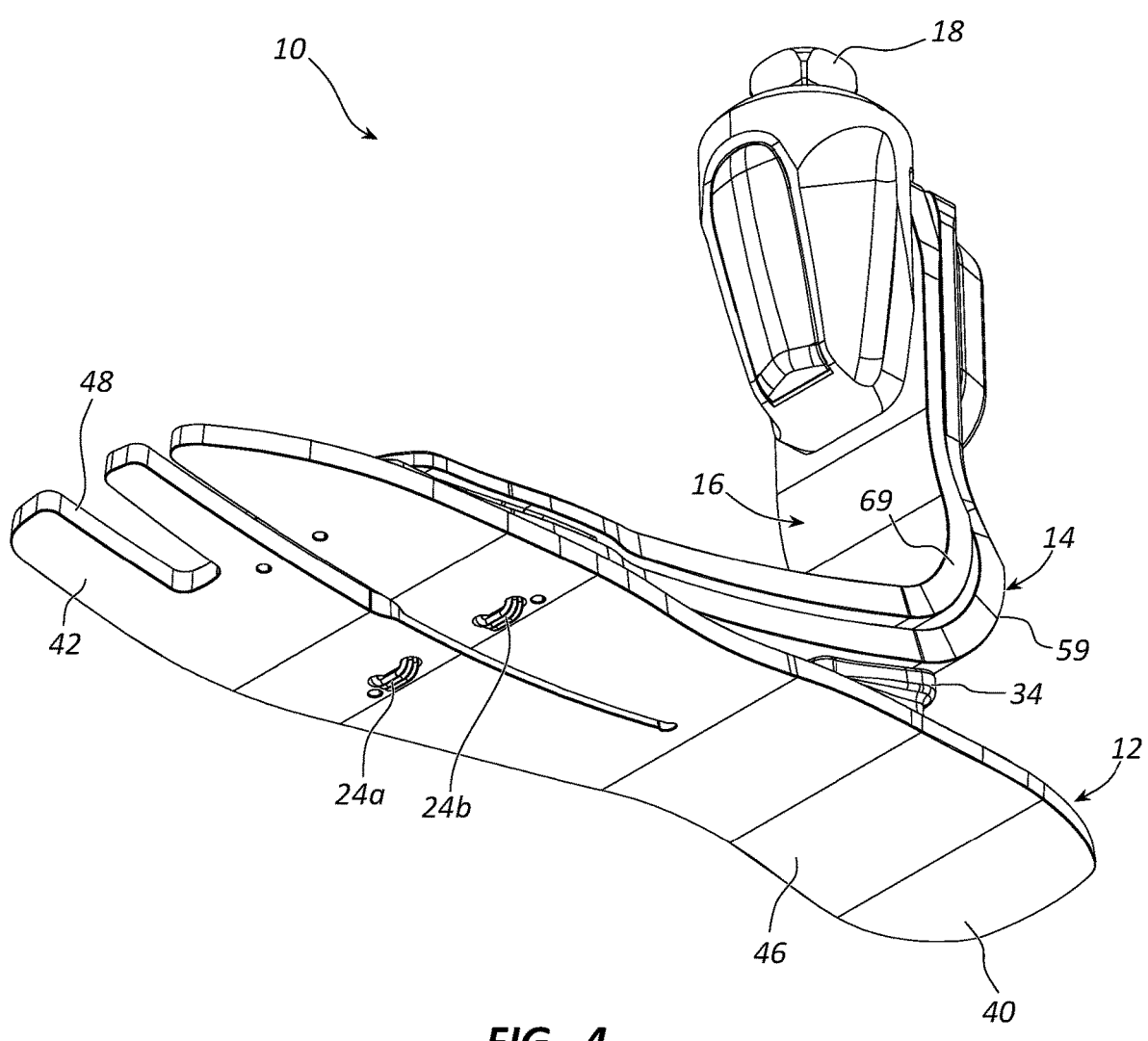
FIG. 4 is a bottom perspective view of the prosthetic foot shown in FIG. 1.
Figure 7:
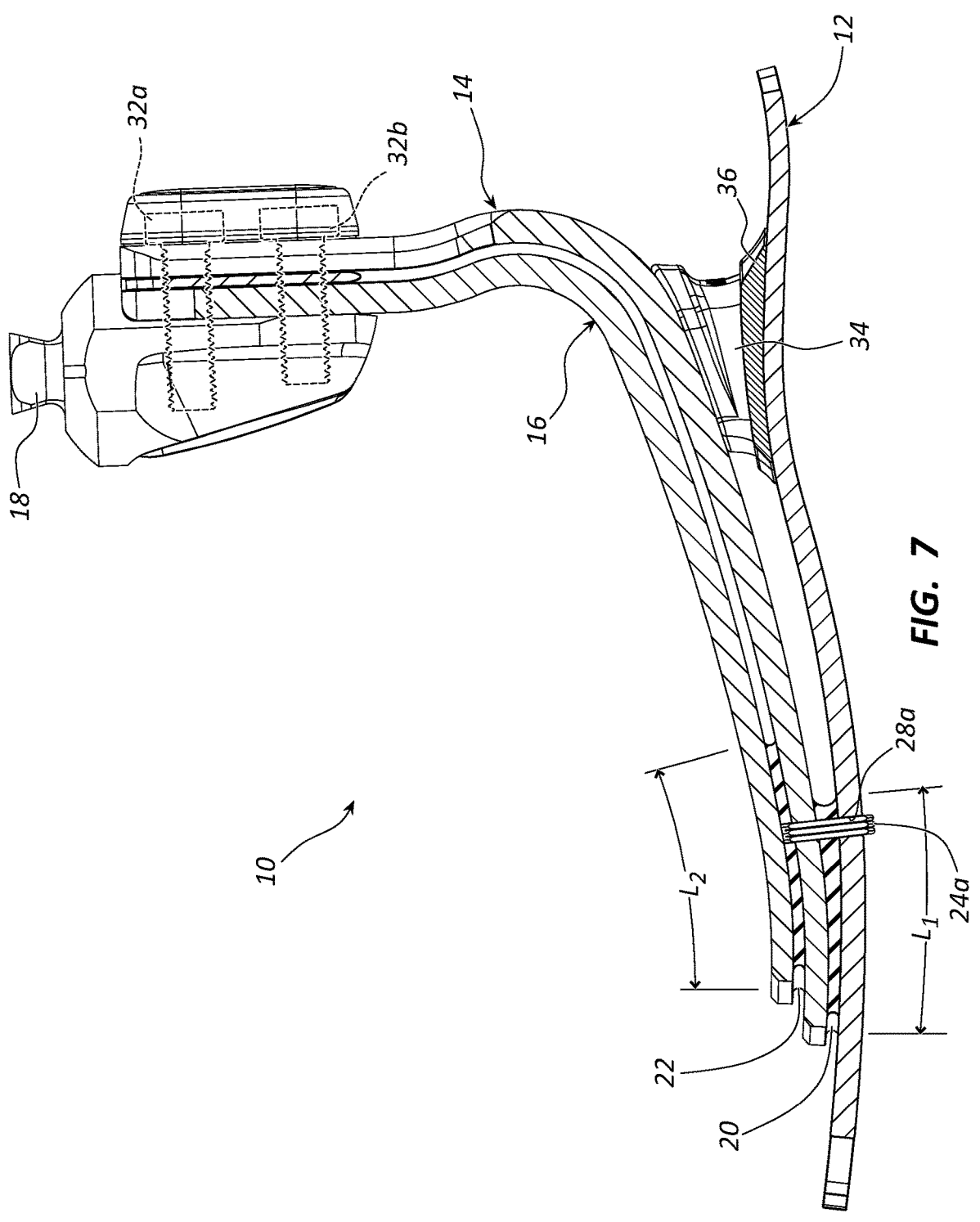
FIG. 7 is a cross-sectional view of the prosthetic foot shown in FIG. 5 taken along cross-section indicators 7-7.
Figure 8:
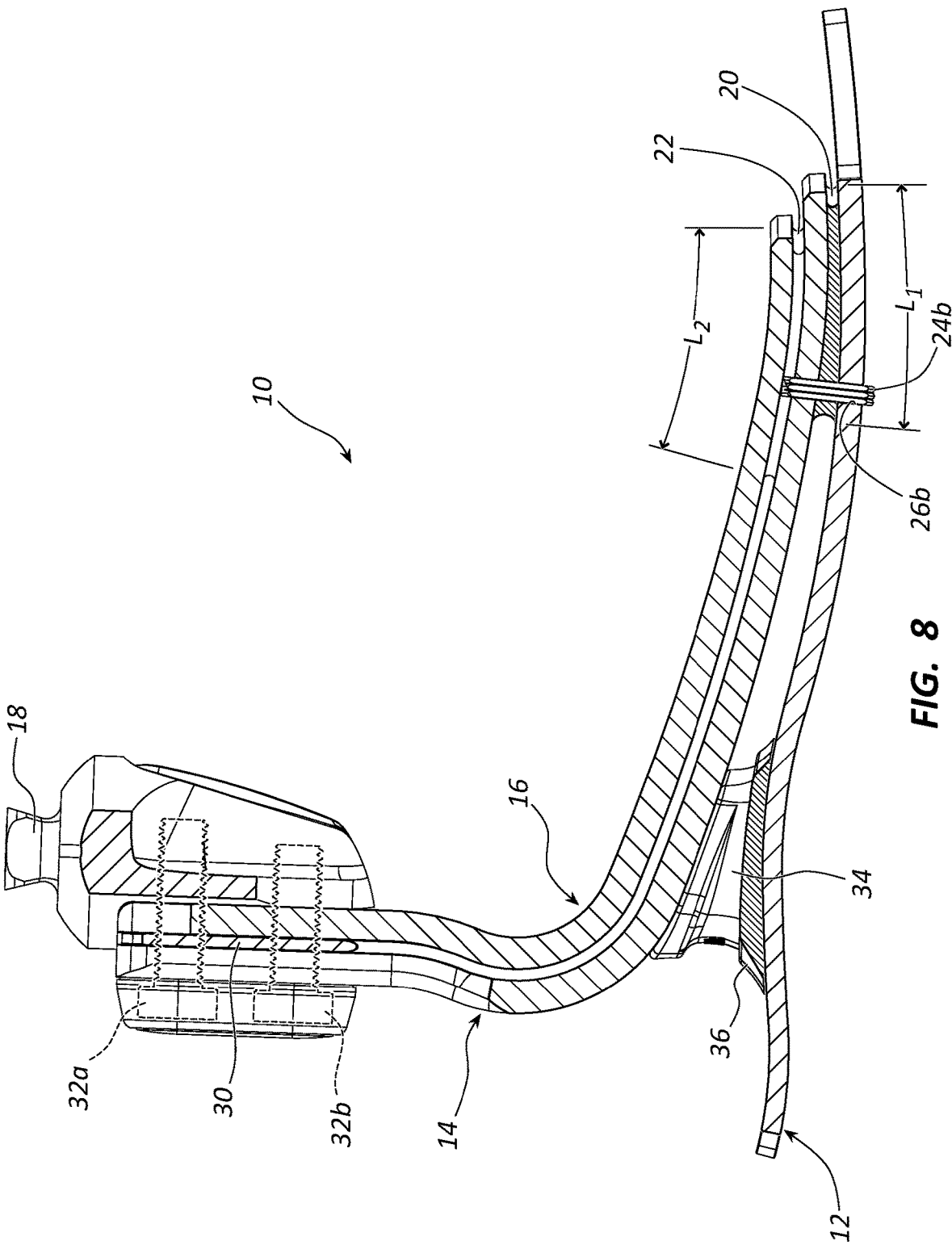
FIG. 8 is a cross-sectional view of the prosthetic foot shown in FIG. 5 taken along cross-section indicators 8-8.

Referring to FIG. 3, the base spring 12 includes a heel end portion 40, a toe end portion 42, top and bottom surfaces 44, 46, and a sandal slot 48. The first and second holes 26a, 28a and third and fourth holes 26b, 28b extend through the base spring 12 as shown in FIG. 2. These same holes are also formed in the first bond connection 20 and the first top spring 14 as shown in FIGS. 7 and 8.

Base spring 12 may include the sandal slot 48 as well as a balance slot 49 as shown in FIG. 2. The balance slot 49 may extend along a centerline of the base spring between the heel and toe end portions 40, 42, or at least along a length dimension of the base spring 12. The sandal slot 48 may be positioned forward of the first and second spring connectors 24a, 24b. The balance slot 49 may extend longitudinally from one side of the spring connectors 24a, 24b to an opposite, rearward side of the spring connectors 24a, 24b. Furthermore, the first spring connector 24a may be positioned on a medial side of the balance slot 49, and the second spring connector 24b may be positioned on a lateral side of the balance slot 49, or vice versa. Positioning the spring connectors 24a, 24b on opposite sides of the balance slot 49 may provide for the desired positive connection between the base spring 12 and at least the first top spring 14 regardless of the relative movement of the lateral and medial sides of the base spring 12 during operation of the prosthetic foot 10.

As shown in at least FIGS. 2-6, the base spring 12 has a contoured shape along its length. The side profile of the base spring 12 shown in FIG. 6 undulates between concave and convex shapes. In some examples, the base spring is preferably convex in an anterior section, transitions to concave in an arc or mid-section, and may transition back to convex at the posterior end. These contours and the location of the contours, particularly relative to the toe end connection provided at the first and second bond connections 20, 22 and the first and second spring connectors 24a, 24b, may provide improved roll over smoothness, enhanced energy feedback to the user, stability, and comfort during use of the prosthetic foot. Providing a lever portion extending posterior of the heel cushion 34 may also provide improved smoothness in the roll over and energy feedback during use.

The first and second top springs 14, 16 in combination with the second bond connection 22 and the spacer 30 may be referred to as a top spring assembly. The top spring assembly may be preassembled (e.g., with the prosthesis connector 18) prior to being mounted to the base spring 12 with the first bond connection 20 and the first and second spring connectors 24a, 24b. Alternatively, the first top spring 14 may be secured to the base spring 12 with the first bond connection 20 and the first and second spring connectors 24a, 24b, followed by securing the second top spring 16 to the first spring connector 14 with the second bond connection 22.

The second bond connection 22 and spacer 30 provide a gap G provided between the first and second top springs 14, 16 along their entire length. The first and second top springs 14, 16 may be referred to as leaf springs. The first and second top springs 14, 16 make extend generally in parallel with each other along their entire lengths.

The second bond connection 22 used to secure the first and second top springs 14, 16 together may comprise the same or similar material that also is used for the first bond connection 20. Typically, the first and second bond connections 20, 22 generally overlap each other in the longitudinal and medial/lateral direction. The first and second bond connections 20, 22 may each be divided along longitudinal centerlines of the first and second top springs 14, 16 to be positioned on opposite sides of the balance slot 49 formed in the base spring 12.

At least FIG. 2 shows the first and second bond connections 20, 22 each divided into separate medial and lateral portions. The first and second bond connections 20, 22 may provide a permanent connection between the first and second top springs 14, 16. The material of the first and second bond connections 20, 22 may provide at least some relative movement between the first and second top springs 14, 16 (i.e., rotational movement about a vertical axis, translational movement and interior/posterior or medial/lateral direction, compression, etc.). The material of the second connection 22 may be elastic so as to return to its original shape upon removal of a force that is used to compress or to form the first and second bond connections 21, 22.

The spacer 30 may comprise a rigid material that is non-compressible and/or non-elastic. The spacer 30 may be positioned at a proximal most end of the first and/or second top spring 14, 16. The spacer 30 may be aligned with the prosthesis connector 18 or at least portions thereof. In some arrangements, the spacer 30 may include apertures through which the fasteners 32a, 32b extend for connection of the prosthesis connector 18 to the first and second top springs 14, 16.

The second bond connection 22 and spacer 30 individually or collectively may define at least in part the size of the gap G between the first and second top springs 14, 16 when the prosthetic foot 10 is in a rest state. Typically, the gap G is provided along an entire length of the first and second top springs 14, 16 when the prosthetic foot 10 is in a rest state (i.e., prior to application of a force during use of the prosthetic foot 10). Alternatively, the first and second top springs 14, 16 may abut (e.g., directly contact each other) at the location of the prosthesis connector 18, for example, if the spacer 30 is removed from the prosthetic foot 10. Typically, the gap G may reduce in size at some locations along the length of the first and second top springs 14, 16 if the material of the second connector 22 is compressible during use. In another example, the gap G may be reduced or change size at locations between the second bond connection 22 and the spacer 30 during use of the prosthetic foot 10. For example, applying a force from a user during a gate cycle may change the size of gap G at various phases of the gate cycle (e.g., at heel stride, stance phase, and toe off). As the forces are applied and released during use by a wearer, those forces are absorbed and/or are fed back through the base spring 12 and heel cushion 34. In at least some embodiments, the first top spring 14 may come into contact with the second top spring 16 during use of the prosthetic foot (i.e., the gap G reduces to zero).

The first top spring 14 is shown having distal and proximal ends 50, 52, top and bottom surfaces 54, 56, and a balance slot 58 (see FIG. 3). The first top spring 14 also has a bend portion 59 located between the distal and proximal ends 50, 52. The bend portion 59 provides a significant change in direction between the generally horizontally aligned distal end 50 and the generally vertically aligned proximal end 52.

The second top spring 16 includes distal and proximal end 60, 62, top and bottom surfaces 64, 66, and a balance slot 68. The second top spring 16 also includes a bend portion 69 positioned between the distal and proximal ends 60, 62. The bend portion 69 provides a significant change in orientation between the generally horizontally position of distal end 50 and the generally vertically positioned proximal end 62. The bend portions 59, 69 may be generally aligned with each other as shown throughout the figures. The bend portions 59, 69 may provide increased bending or flexure within the prosthetic foot 10 between the connection points provided by the first and second bond connections 20, 22 between the base spring 12 and the prosthesis connector 18.

The balance slots 58, 68 may extend along a longitudinal centerline of the first and second top springs 14, 16, respectively. The balance slots 58, 59 may also be aligned with the balance slot 49 of the base spring 12. The balance slots 58, 68 may extend from a location at the distal ends 50, 60 to a location spaced proximal of the first and second spring connectors 24a, 24b. In other embodiments, one or both of the first and second top springs 14, 16 may be void of a balance slot. Alternatively, one or both of the first and second top springs 14, 16 may include a balance slot that terminates distal or forward of the first and second spring connectors 24a, 24b. Furthermore, the base spring 12 may be void of a balance slot 49, or may include a balance slot that terminates distal or forward of the first and second spring connectors 24a, 24b. In such embodiments in which there is no balance slot provided in the base spring 12 and first and second top springs 14, 16, the prosthetic foot 10 may include only a single one of first and second spring connectors 24a, 24b. Furthermore, one or more of the first and second spring connectors 24a, 24b may be positioned at other locations besides being positioned side-by-side as shown in FIGS. 1-8. Alternative arrangements for the spring connectors are described below with reference to FIGS. 17-20C.

The base spring 12 and first and second top springs 14, 16 may each comprise a fiber-reinforced composite material, such as, for example, carbon fiber reinforced composite. Other materials are possible for the springs 12, 14, 16 such as thermoplastic matrix composites and fiberglass, basalt, or aramid fiber composites. The first and second bond connections 20, 22 may include an adhesive bond comprising a flexible adhesive such as, for example, a urethane adhesive having a Shore A hardness in the range of about 70 to about 95. During manufacture of the prosthetic foot 10, the first and second top springs 14, 16 may be bonded together using a removable gasket between the springs to create a sealed space for the adhesive, and the adhesive is then injected into the space. Similarly, when the first top spring 14 is assembled with the base spring 12, the springs 12, 14 may be bonded together using a removable gasket between the springs to create a sealed space for the adhesive, and then the adhesive is then injected into the space between the springs 12, 14.

Typically, the first and second spring connectors 24a, 24b are connected to the base spring 12 and first top spring 14 after the first bond connection 20 is formed to connect the base spring 12 and first top spring 14 together. The pairs of holes 26, 28 are formed through the base spring 12, first top spring 14 and first bond connection 20 followed by inserting the first and second spring connectors 24a, 24b through the pairs of holes. In some arrangements, the pairs of holes 26, 28 are formed using, for example, conventional drilling, melting a thermoplastic material, laser or abrasive drilling, or forming a composite material around pins located on a mold surface. Once the holes are formed, the first and second spring connectors 24a, 24b are fed through the holes and the first and second connectors 24a, 24b are separately formed in loop-shaped structures with opposing ends connected to each other to provide a continuous loop. The first and second spring connectors 24a, 24b may comprise any of a variety of different materials in different constructions. In one example, the first and second spring connectors 24a, 24b comprise, for example, one or more of a thread, a string, a strand, a cord, a tow, a roving, a braid, a lashing, and a cable. Generally, the spring connectors have an elongate shape. The spring connectors may comprise a flexible material selected, for example, from one or more of polyester, nylon, Kevlar®, Dyneema®, Spectra®, and a metal fiber. The spring connectors may be inextensible along their length while still being flexible to take on different shapes such as the loop shape structure mentioned above. An inextensible spring connector may have a fixed length or be inflexible in the length direction while being flexible in dimensions to take on different shapes.

Figure 6:
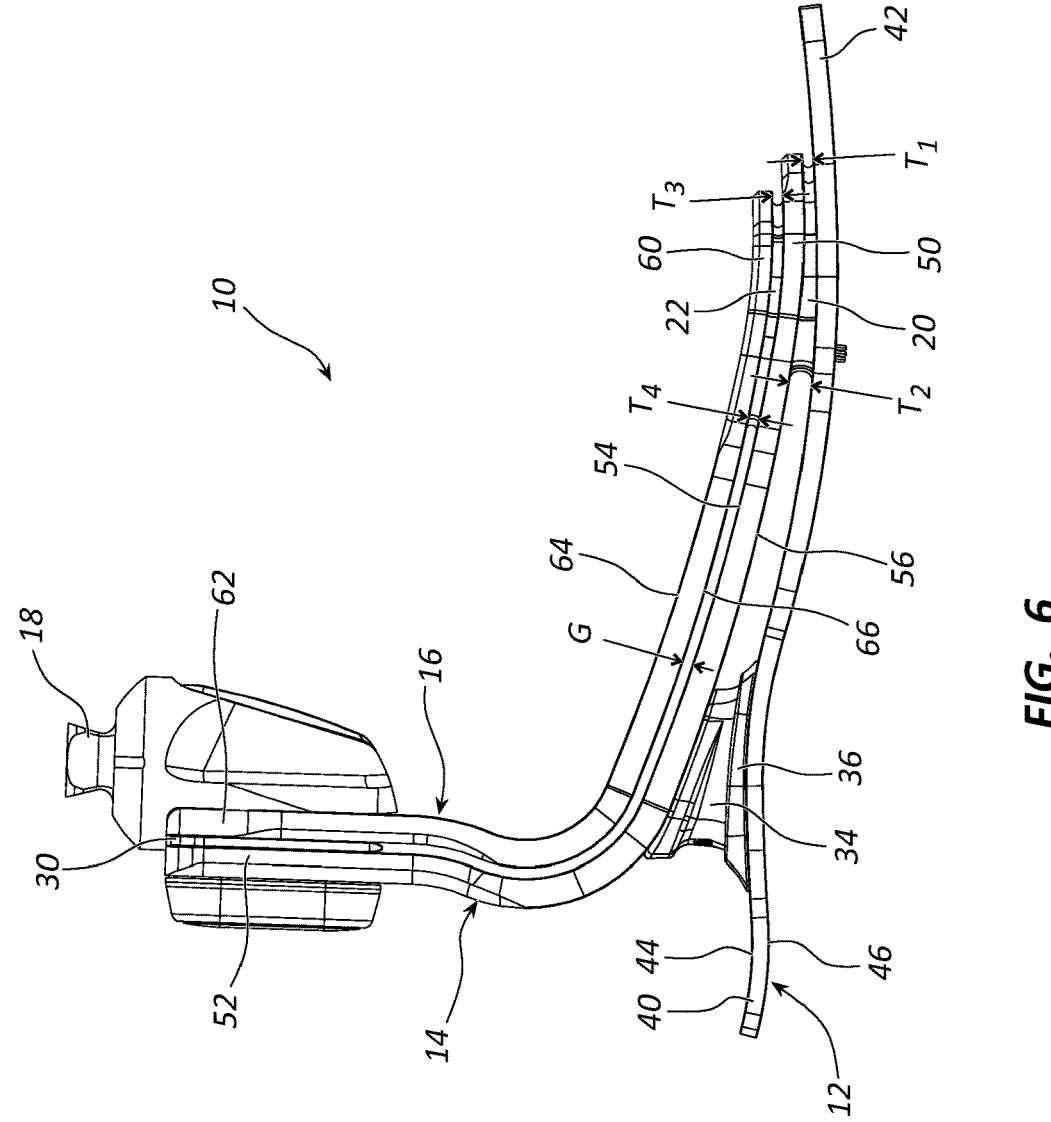
FIG. 6 is a right side view of the prosthetic foot shown in FIG. 1.
Figure 5:
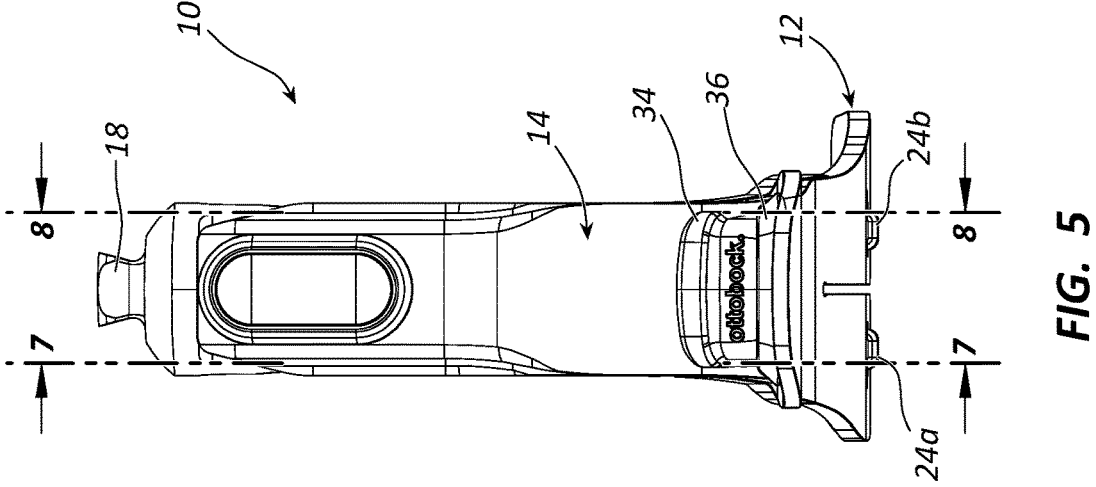
FIG. 5 is a rear view of the prosthetic foot shown in FIG. 1.

The first bond connection 20 may have front and rear thicknesses $T_1$, $T_2$ and a length $L_1$ as shown in FIGS. 6 and 7. The second bond connection 22 may have front and rear thicknesses $T_3$, $T_4$ and a length $L_2$ as also shown in FIGS. 6 and 7. The length $L_1$ of the first bond connection 20 may be significantly reduced when using the spring connectors 24a, 24b. Without the use of the spring connectors 24a, 24b, the length $L_1$ typically must extend further rearward to provide an adequate connection that will reduce the likelihood of failure of the first bond connection 20. However, extending the length $L_1$ also reduces the flexibility properties and other spring characteristics of the base spring 12 and first top spring 14. Thus, the use of the spring connectors 24a, 24b provides for a reduced length $L_1$ of the first bond connection 20, thereby maximizing the performance characteristics of the base spring 12 and first top spring 14. In some embodiments, the length $L_1$ may be less than the length $L_2$. As described below, the length $L_1$ may be equal to or greater than a length $L_2$ in embodiments where the spring connectors 24a, 24b extend through both the first and second top springs 14, 16 (see FIGS. 9-16).

Figure 9:
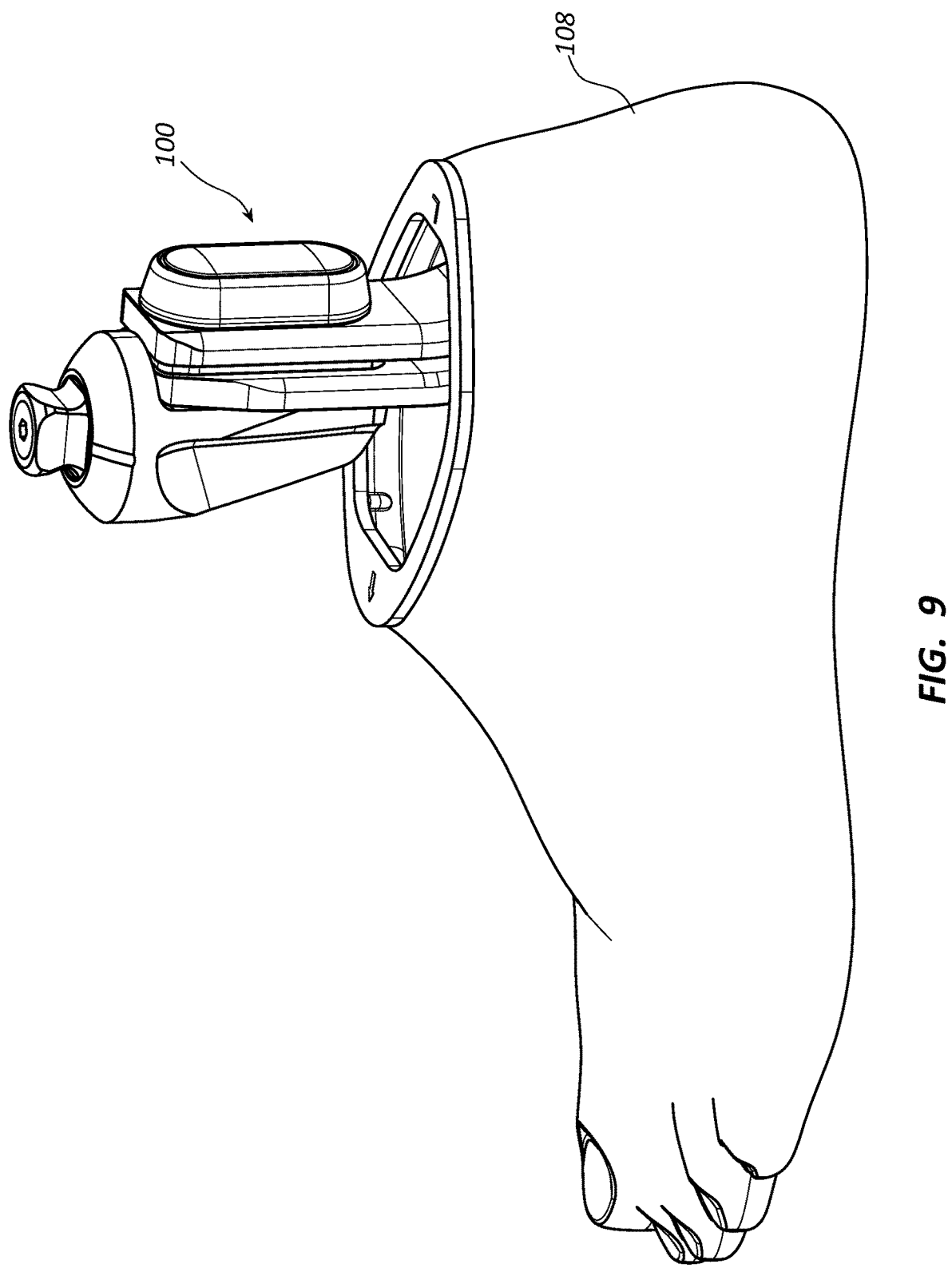
FIG. 9 is a side perspective view of an example prosthetic foot assembly in accordance with the present disclosure.

Referring now to FIGS. 9-16, another example prosthetic foot 100 is shown with the foot casing 8 (see FIG. 9). The prosthetic foot 100 includes a base spring 112, first and second top springs 114, 116, a prosthesis connector 118, first and second bond connections 120, 122, first and second spring connectors 124a, 124b, pairs of holes 126a, 128a and 126b, 128b, a spacer 130, and fasteners 132a, 132b. The prosthetic foot 100 also includes the heel cushion 134 and associated heel cushion seat 136. The prosthetic foot 100 has the same or similar features as the prosthetic foot 10 described above with exception of the arrangement for the first and second spring connectors 124a, 124b and the pairs of holes 126, 128. In the prosthetic foot 100, the holes 126, 128 extend through the base spring 12, first and second top springs 114, 116, and first and second bond connections 120, 122. The spring connectors 124a, 124b also extend through the springs 112, 114, 116 and the bond connections 120, 122 to provide a positive connection there between.

Figure 15:
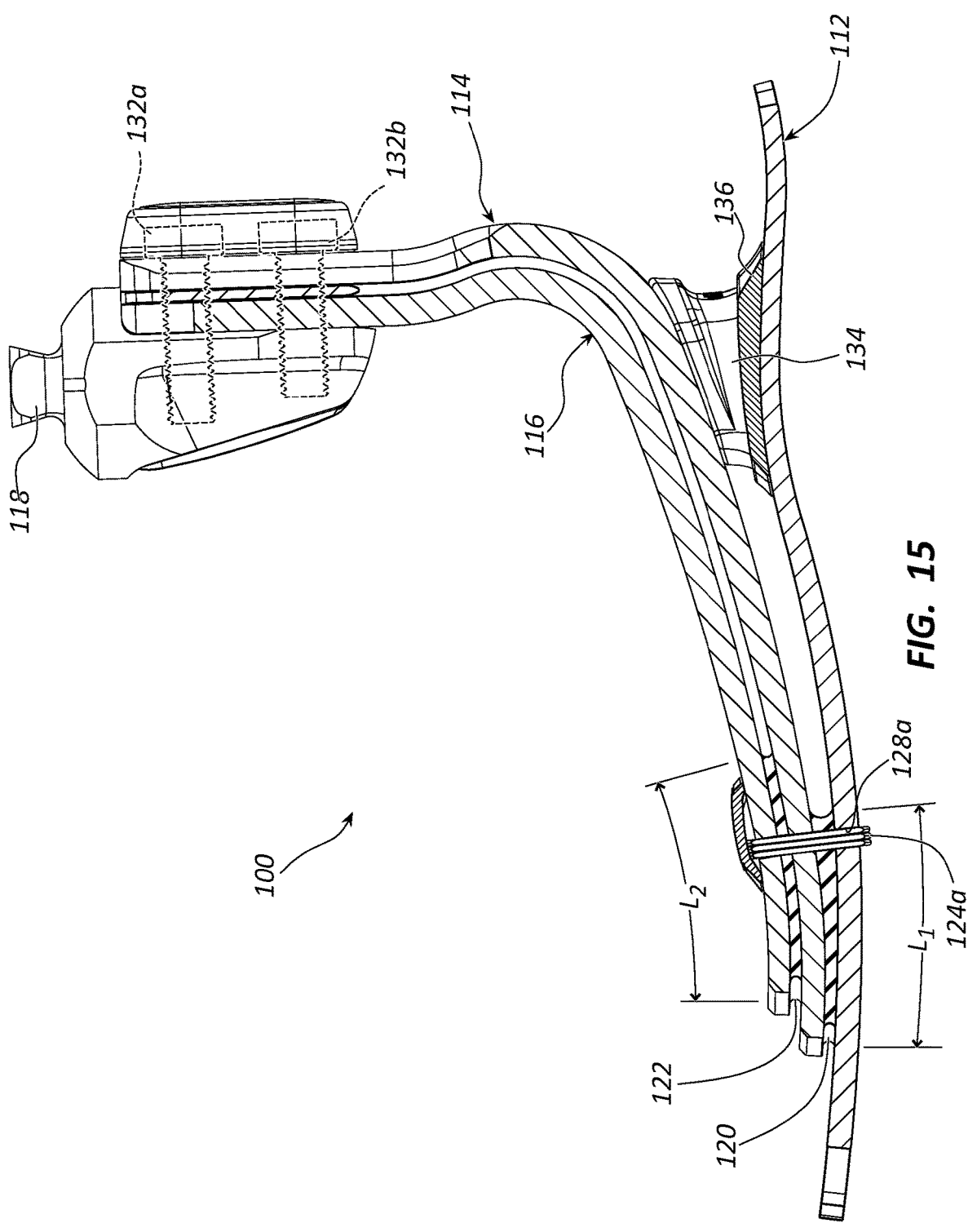
FIG. 15 is a cross-sectional view of the prosthetic foot shown in FIG. 13 taken along cross-section indicators 15-15.
Figure 16:
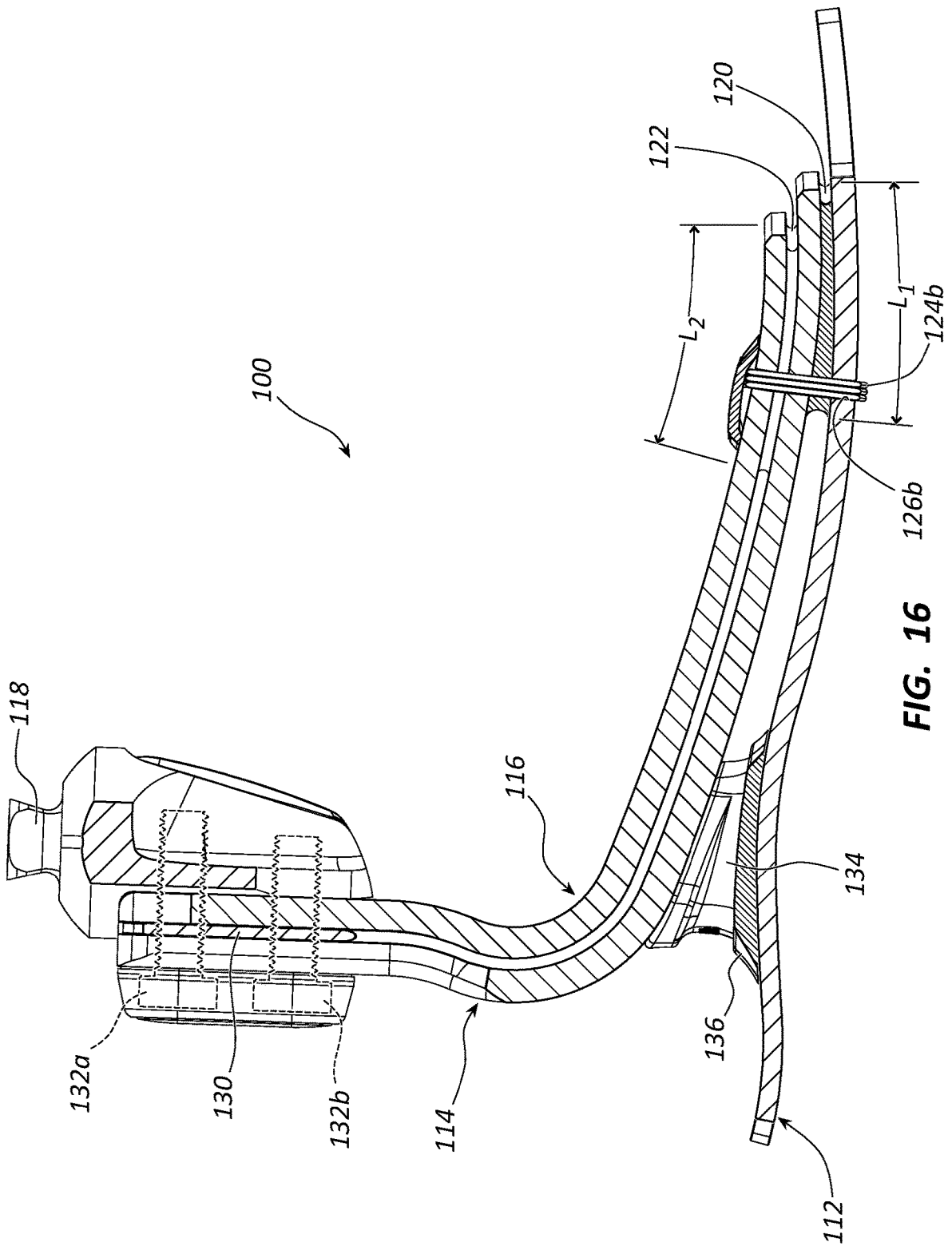
FIG. 16 is a cross-sectional view of the prosthetic foot shown in FIG. 13 taken along cross-section indicators 16-16.

Typically, the base spring 112 is connected to the first top spring 114 with the first bond connection 120 and the second top spring 116 is connected to the first top spring 114 with the second bond connection 122. The pairs of holes 126, 128 are formed to provide a path for the first and second spring connectors 124a, 124b to extend between all of the components 112, 114, 116, 120, 122. As with the spring connectors 24a, 24b described above, the spring connectors 124a, 124b are formed into a continuous loop-shaped structure that provides the desired positive connection. Typically, the spring connectors 124a, 124b are positioned towards a rear or posterior end of the first and second bond connections 120, 122 as shown in FIGS. 15 and 16. The spring connectors 124a, 124b may provide a secondary connection in addition to the primary connection provided by the bond connections 120, 122.

Figure 10:
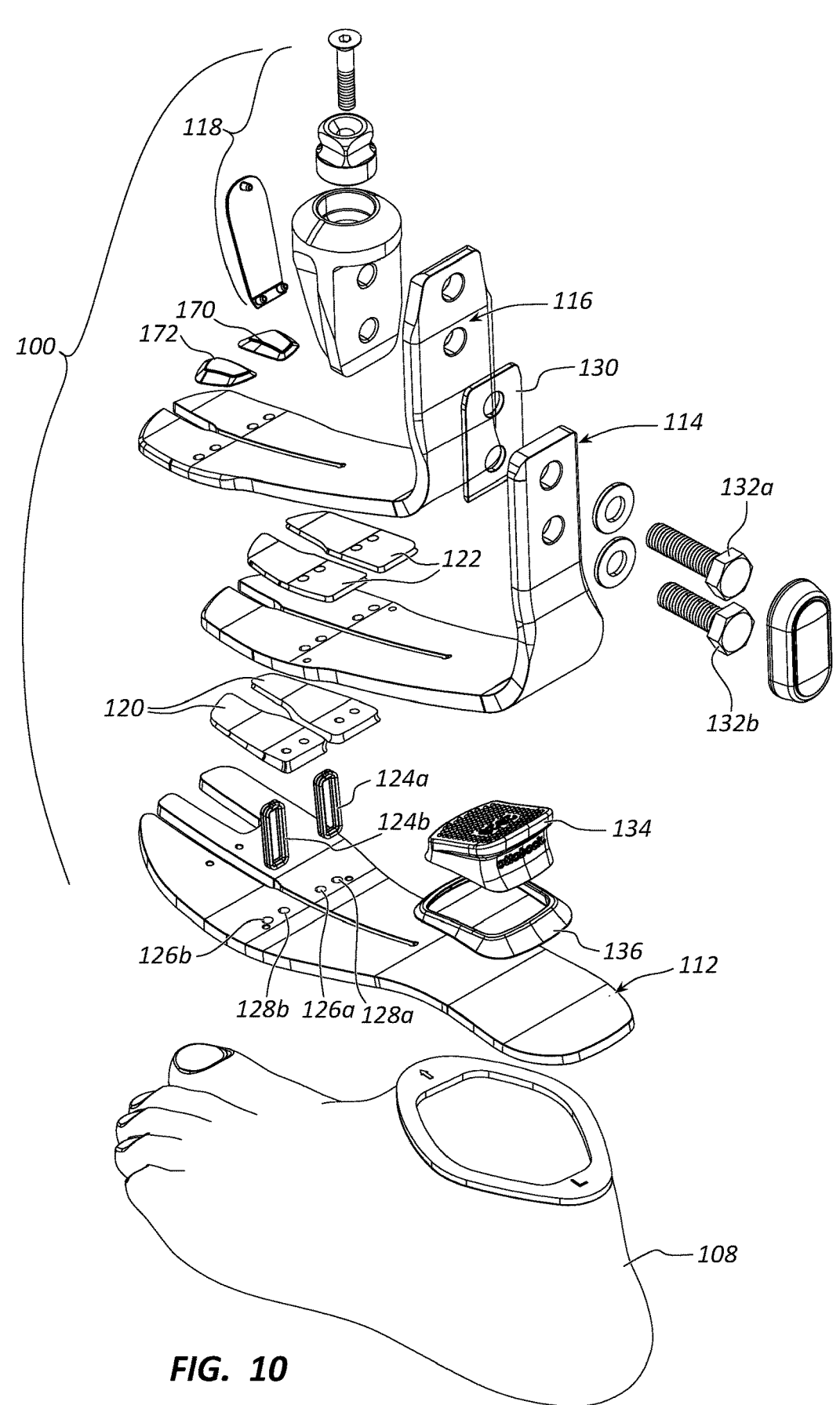
FIG. 10 is an exploded perspective view of the prosthetic foot assembly shown in FIG. 9.
Figure 11:
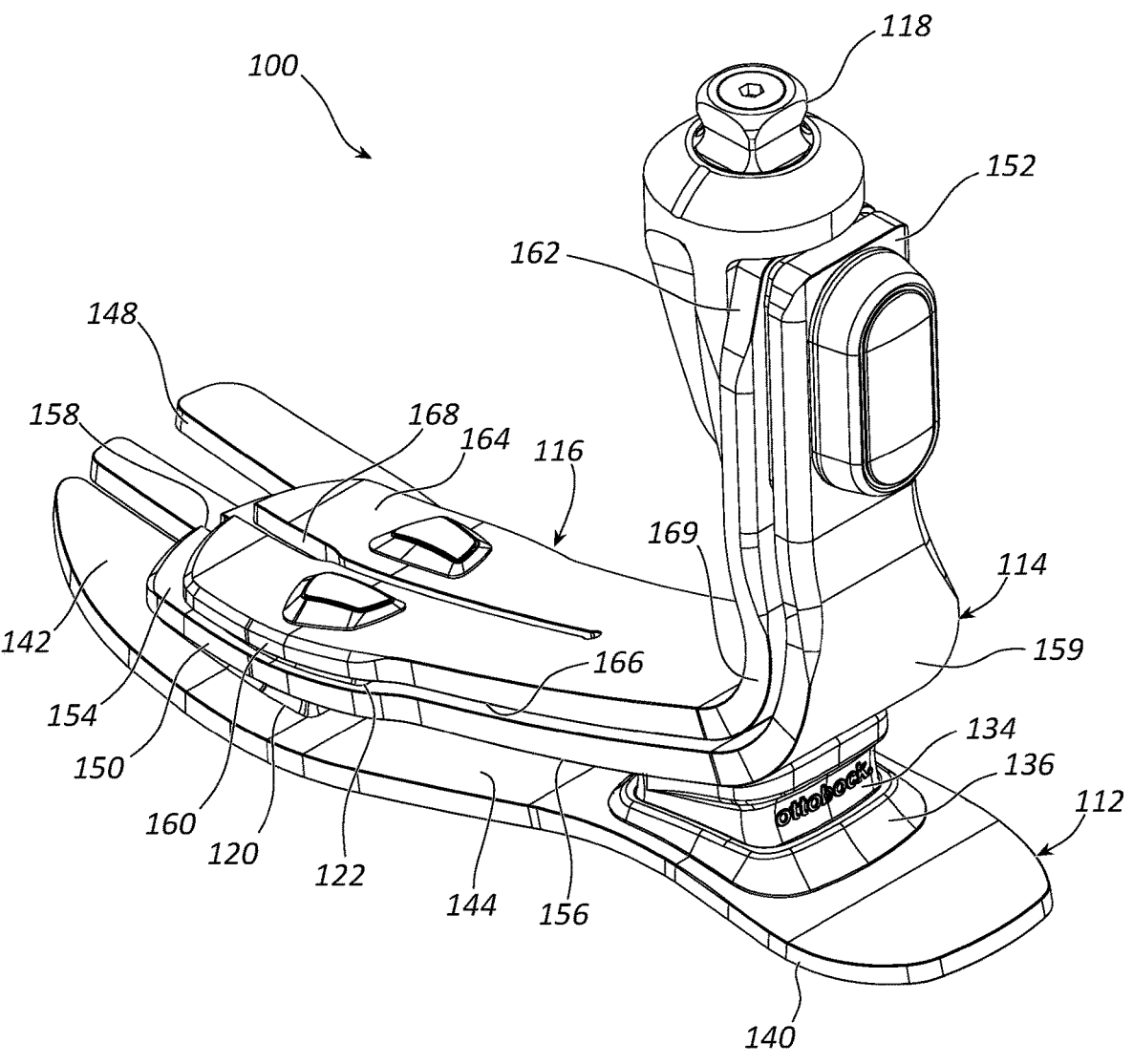
FIG. 11 is a rear perspective view of a prosthetic foot shown in FIG. 9.
Figure 12:
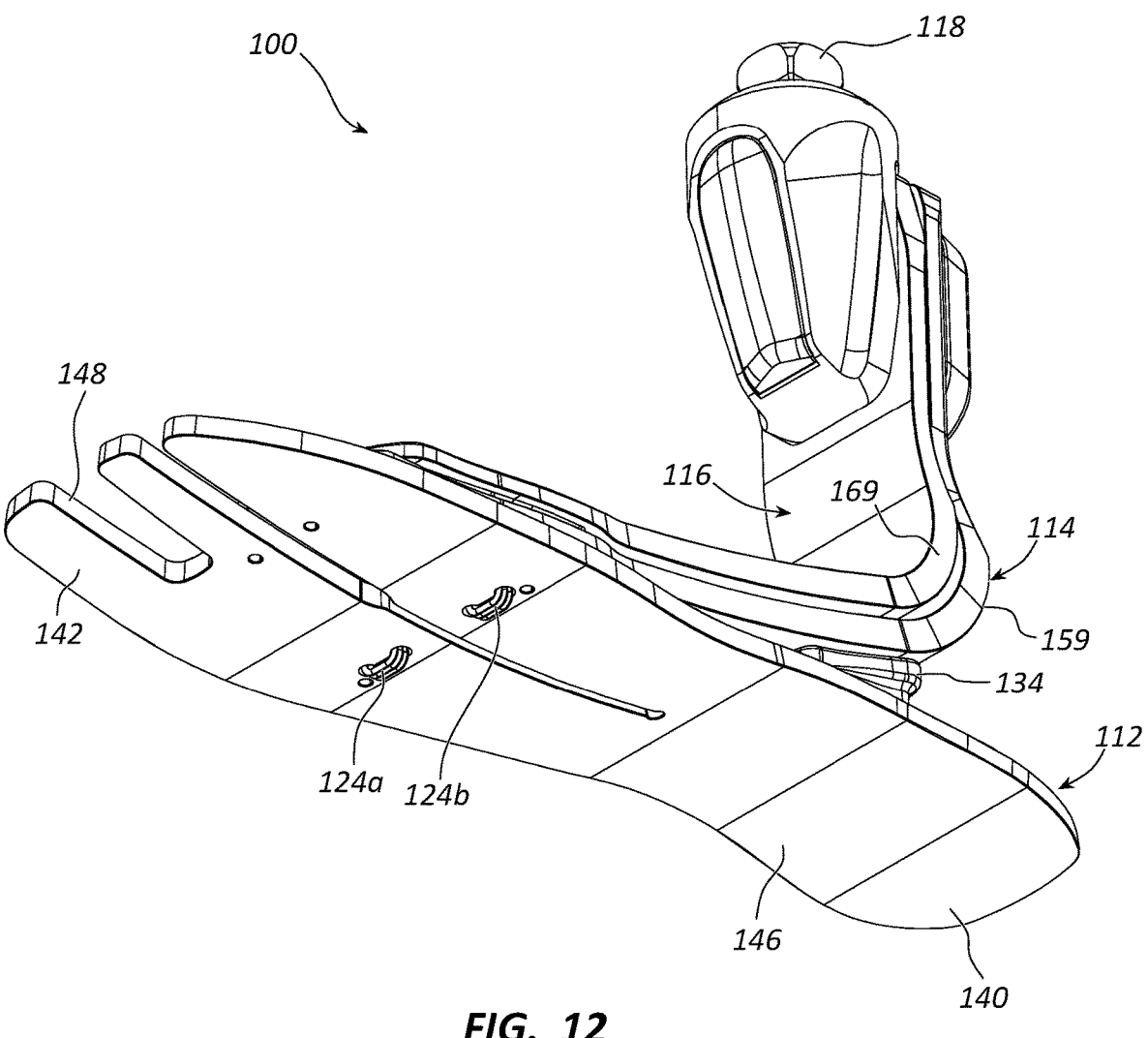
FIG. 12 is a bottom perspective view of a prosthetic foot shown in FIG. 9.
Figures 13, 14:
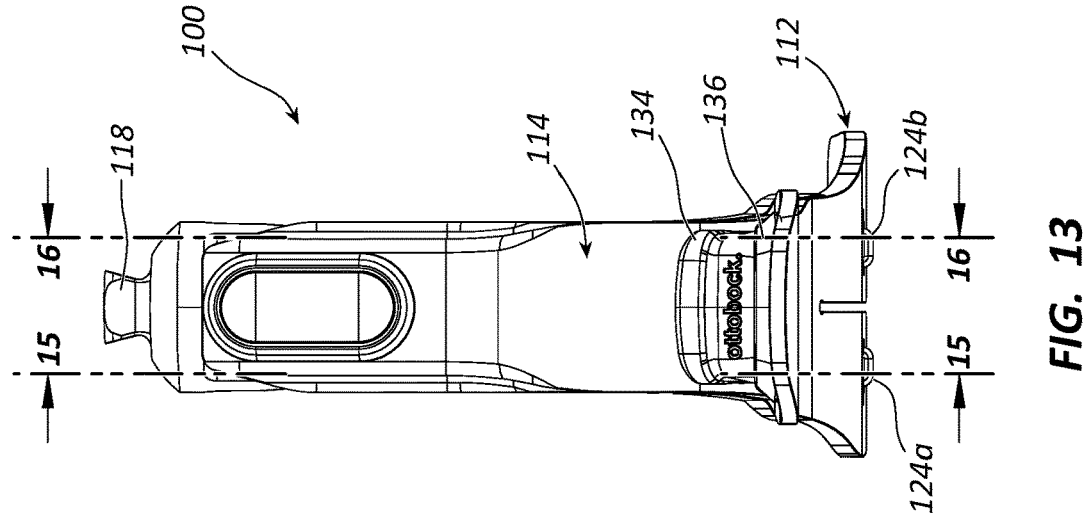
FIG. 13 is a rear view of the prosthetic foot shown in FIG. 9.
FIG. 14 is a right side view of the prosthetic foot shown in FIG. 9.

Furthermore, the spring connectors 124a, 124b may be covered along the top surface of the second top spring 116 with covers 170, 172 (see FIGS. 10-12). The covers 170, 172 may provide a more aesthetically pleasing appearance for the prosthetic foot 100. The covers 170, 172 may also reduce the incidence of wear or damage to the spring connectors 124a, 124b.

The base spring 112 includes heel and toe end portions 140, 142, top and bottom surfaces 144, 146, a sandal slot 148, and a balance slot 149 (see FIGS. 11 and 12). The first top spring 14 includes distal and proximal ends with 150, 152, top and bottom surfaces 154, 156, a balance slot 158 and a bend portion 159. The second top spring 116 includes distal and proximal ends 160, 162, top and bottom surfaces 164, 166, a balance slot 168, and a bend portion 169. The first bond connection 120 includes front and rear thicknesses $T_1$, $T_2$ and a length $L_1$. The second bond connection 122 includes front and rear thicknesses $T_3$, $T_4$ and a length $L_2$ (see FIGS. 14 and 15).

The thicknesses $T_1$-$T_4$ may change for the prosthetic feet 10, 100 during use giving the flexible nature of the first and second bond connections. The use of one or more spring connectors 24*a*, 24*b* and 124*a*, 124*b* may influence the change in thickness to T$_1$-T$_4$ during use of the prosthetic feet 10, 100. For example, the thickness T$_4$ in the prosthetic foot 100 may have a greater range of size as compared to the thickness T$_4$ in the prosthetic foot 100 because the spring connectors 124*a*, 124*b* fix a maximum spacing between the second top spring 116 and the base spring 112. In some embodiments, the spring connectors may hold one or both of the bond connections in compression when the prosthetic foot is in a rest state, thereby, further influencing the range of change for any one of the thicknesses T$_1$-T$_4$. Further, the length L$_2$ for the prosthetic foot 100 may be reduced as compared to the length L$_2$ for the prosthetic foot 10 because the spring connectors 124*a*, 124*b* secure the second top springs 116 to the base spring 112. In at least some arrangements, the length L$_2$ may be the same or smaller than the length L$_1$ in the prosthetic foot 100.

The thicknesses T$_1$-T$_4$ may be at least as great as a diameter or maximum width/thickness of the spring connectors 24*a*, 24*b* in the embodiment of FIGS. 1-8. Typically, the thicknesses T$_1$-T$_4$ are greater than the maximum diameter and/or width of the spring connectors 24*a*, 24*b* such that the second top spring 16 does not come into contact with the spring connectors 24*a*, 24*b*, even when the second bond connection 22 is compressed. In other embodiments, the first top spring 14 includes recesses or grooves along the top surface thereof adjacent to the pairs of holes 26, 28. Such recesses or grooves may be sized and shaped to accommodate the spring connectors 24 for the embodiment of FIGS. 1-8 (e.g., such that the spring connectors 24 are flush with the top surface of the first top spring 14). Similar recesses or grooves may be formed in the top surface of the second top spring 16 to accommodate the spring connectors for the embodiment of FIGS. 9-16.

In some embodiments, the thicknesses T$_1$-T$_4$ have a minimum size of at least 0.05 inches. Such a minimum thickness provides the desired flexible properties of the bond connection for most types of bonding materials (e.g., those materials listed above for the bond connections). The thicknesses T$_1$-T$_4$ may also have a maximum thickness in the range of about 0.1 to about 1.0 inches, and more particularly about 0.5 inches. Such a maximum thickness limits the total height of the prosthetic foot in the forefoot area, which may have certain advantages such as flexibility in the medial-lateral direction. In general, the flexibility of the joint increases with increasing thickness, while in general stiffer materials have increased strength. Hence, a thicker bond connection may be used to increase the strength while maintaining a desired flexibility in the joint.

The prosthetic feet described here may include covers for the spring connectors positioned along the bottom surface of the base spring 12. Such covers may provide protection against wear and/or damage for the spring connectors along the bottom side of the prosthetic foot. In other embodiments, the base spring 12 includes recesses or grooves along the bottom surface thereof adjacent to the pairs of holes 26, 28. Such recesses or grooves may be sized and shaped to accommodate the spring connectors 24 (e.g., such that the spring connectors 24 are flush with the bottom surface of the base spring).

In the embodiments shown in FIGS. 1-16, the spring connectors are positioned in a way that extends through the first and second bond connections (i.e., overlapping and extending through the bond connections). In other embodiments, these spring connectors may be positioned rearward/posterior of one or both of the first and second bond connections. Although not preferred, it may be possible to position one or more spring connectors at a location space forward/anterior of one or both of the first and second bond connections. In certain designs, it may be advantageous to connect two or more components of an upper spring assembly using spring connectors without using any spring connectors to connect a base spring to the upper spring assembly.

Referring now to FIGS. 17-20, several alternative spring connector embodiments are shown in cross section. Although the spring connectors are shown extending through the base spring and first and second top springs, other embodiments are possible in which the spring connectors extend through only the base spring and first top spring, through the first and second top springs and not the base spring, or extend through the base spring and three or more top springs. Furthermore, the spring connectors shown in FIGS. 17-20 extend through at least the first bond connection and in most instances the second bond connection as well. Other embodiments may include the spring connector arrangements of FIGS. 17-20 when using one or both of the first and second bond connections. Further, the spring connectors may pass through two or more springs (e.g., the base spring and first top spring) and not pass through a bond connection. For example, the spring connector may extend through apertures formed in two or more spring while also being arranged adjacent to a bond connection that is used to secure the two or more springs together without passing through a hole or aperture formed in the bond connection.

Figures 17, 18, 19, 20:
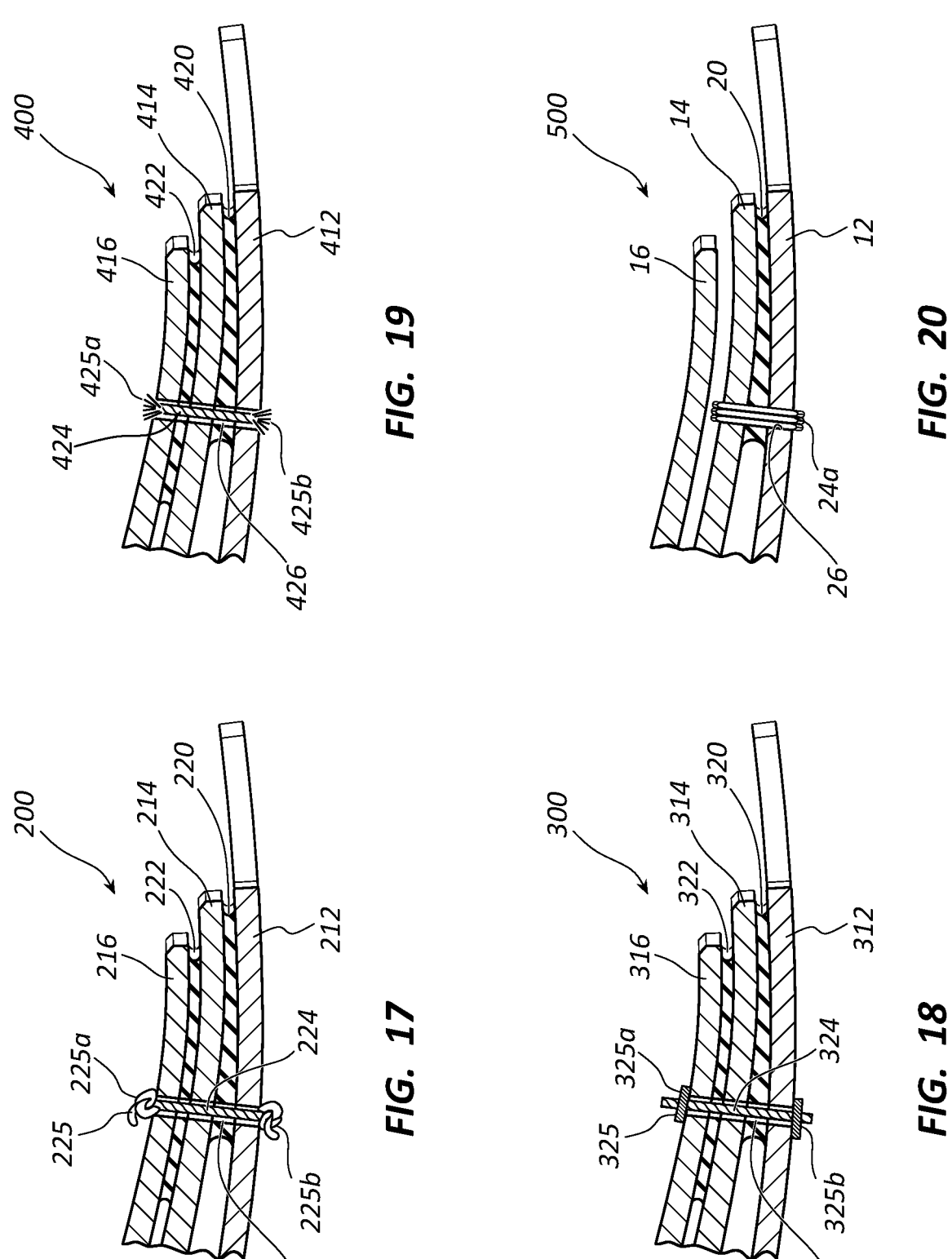
FIG. 17 is a cross-sectional view of a portion of another prosthetic foot in accordance with the present disclosure.
FIG. 18 is a cross-sectional view of a portion of another prosthetic foot in accordance with the present disclosure.
FIG. 19 is a cross-sectional view of a portion of another prosthetic foot in accordance with the present disclosure.
FIG. 20 is a cross-sectional view of a portion of another prosthetic foot in accordance with the present disclosure.

FIG. 17 shows a prosthetic foot 200 including a base spring 212, first and second top springs 214, 216, first and second bond connections 220, 222, and a spring connector 224. Spring connector 224 extends through a hole or aperture 226 formed through all of the members 212, 214, 216, 220, 222. Spring connector 224 may include knots 225*a*, 225*b* formed in the spring connector 224 and positioned at opposite top and bottom sides of the prosthetic foot 200. The knots 225*a*, 225*b* may help hold the spring connector 224 from being removed from the aperture 226 while securing the springs 212, 214, 216 together as an assembly. The spring connector 224 may be provided as a single elongate, linear strand with the knots 225*a*, 225*b* formed in opposite free ends of the strand.

In some embodiments, the hole or aperture 226 may be formed in the base spring 212 and first and second top springs 214, 216, but not formed in the first and second bond connections 220, 222. The spring connector 224 may then extend through the hole or aperture 226 and not through the first and/or second bond connection 220, 222.

FIG. 18 shows a prosthetic foot 300 including a base spring 312, first and second top springs 314, 316, first and second bond connections 320, 322, and a spring connector 324 that extends through a hole or aperture 326 formed in all of the members 312, 314, 316, 320, 322. The spring connector 324 is provided as a single elongate, linear strand. Spring connector 324 is held in place with members 325*a*, 325*b* that are positioned on opposite top and bottom sides of the prosthetic foot 300. The members 325*a*, 325*b* may be secured to the spring connector 324 in a way to retain a specific position along the length of the spring connector 324. In one example, the members 325*a*, 325*b* are crimped or otherwise secured to the spring connector 324*a* with an interference fit. Other connections include a weld or an adhesive bond. The members 325*a*, 325*b* may be in the form of sleeves, collars, clasp, bead, or other fasteners. The members 325*a*, 325*b* may help hold the spring connector 324 from being removed from the hole 326 while securing the springs 312, 314, 316 together as an assembly.

In some embodiments, the hole or aperture 326 may be formed in the base spring 312 and first and second top springs 314, 316, but not formed in the first and second bond connections 320, 322. The spring connector 324 may then extend through the hole or aperture 326 and not through the first and/or second bond connection 320, 322.

FIG. 19 shows a prosthetic foot 400 that includes a base spring 412, first and second top springs 414, 416, and first and second bond connections 420, 422. A spring connector 424 extends through a hole or aperture 426 that extends through each of the members 412, 414, 416, 420, 422. The spring connector 424 may comprise a plurality of fibers such as a braided fiber structure. The free ends of the spring connector 424 at opposite top and bottom sides of the prosthetic foot 400 may be frayed or expanded in order to have a greater diameter as compared to the remaining portion of the spring connector 424 extending through the hole 426. These frayed ends 425a, 425b may be filled with an adhesive or bonding agent that holds the frayed ends in the expanded position, thereby preventing the frayed end to pass through the hole 426. The base spring 412 and/or second top spring 416 may include grooves or recesses 480 that are sized to receive the frayed ends when in the expanded position. These recesses or grooves 480, 482 may also provide the frayed ends flush or near flush mounted across the bottom surface of the base spring 412 and/or the top surface of the second top spring 416, respectively. The frayed ends 425a, 425b may help hold the spring connector 424 from being removed from the hole 426 while securing the springs 412, 414, 416 together as an assembly.

In some embodiments, the hole or aperture 426 may be formed in the base spring 412 and first and second top springs 414, 416, but not formed in the first and second bond connections 420, 422. The spring connector 424 may then extend through the hole or aperture 426 and not through the first and/or second bond connection 420, 422.

FIG. 20 shows a prosthetic foot 500 having a base spring 12, first and second top springs 14, 16, a bond connection 20, a spring connector 24, and a hole 26 that extends through the base spring 12, first top spring 14, and first bond connection 20. In other embodiments, the hole 26 may extend through the base spring 12 and first top spring 14 and not extend through the first bond connection 20 (e.g., such that the spring connector 24 is positioned adjacent to but not extending through the first bond connection). The prosthetic foot 500 is missing the bond connection 22 shown in FIGS. 1-8. The spring connector 24a may have a thickness or diameter that provides a spacing between the first and second top springs 14, 16. Alternatively, the top surface of the first top spring 14 may include a groove or recess to accommodate the spring connector 24a so that the spring connector 24a is flush with the top surface of the first top spring 14. Accordingly, the second top spring 16 may be positioned in contact with the top surface of the first top spring 14 (e.g., when the prosthetic foot 500 is in a rest position). The spring connector 24a may have the same loop structure shown in FIGS. 1-8. Alternatively, the spring connector 24a may have a single, elongate, linear strand shape as shown in FIGS. 17-19. Further, any of the embodiments shown in FIGS. 17-20 may include multiple spring connectors that interconnect the various springs of the prosthetic feet. The spring connectors may be positioned at any desired location relative to the bond connections, the distal or forwardmost ends of the springs, or to other spring connectors on the prosthetic foot.

Figures 21A, 21B, 21C:
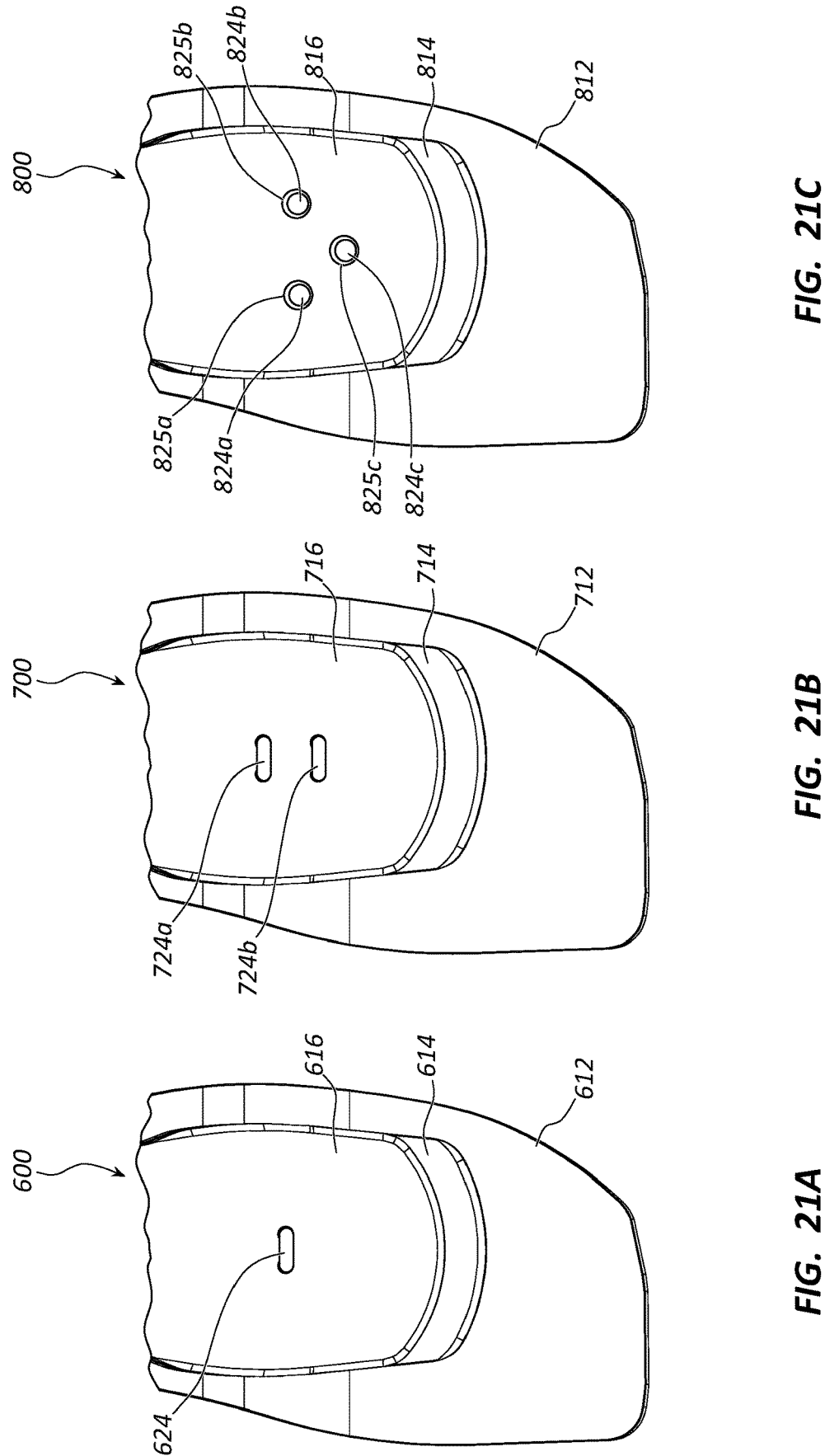
FIGS. 21A-C are top views of a portion of alternative prosthetic feet in accordance with the present disclosure.

FIGS. 21A-C illustrate additional alternative orientations for the spring connectors. FIG. 21A shows a prosthetic foot 600 that includes a base spring 612, first and second top springs 614, 616, and a spring connector 624. The springs 612, 614, 616 may be void of a sandal slot and/or balance slot. Accordingly, the spring connector 624 may be positioned generally along a longitudinal centerline of the prosthetic foot, which may be aligned with the longitudinal centerline of one or more of the springs 612, 614, 616. The spring connector 624 may be positioned at any desired position along the length of the prosthetic foot 600. In some embodiments, the spring connector 624 is positioned adjacent to a proximal or rearward end portion of any bond connection provided between any one of the springs 612, 614, 616. In other arrangements, the spring connector 624 pass through one or more bond connections provided between any of the springs 612, 614, 616. Furthermore, the spring connector 624 may be positioned in any desired location in the lateral direction relative to a centerline of the prosthetic foot 600 extending in a longitudinal direction.

FIG. 21B shows a prosthetic foot 700 with base spring 712, first and second top springs 714, 716, and first and second spring connectors 724a, 724b. The spring connectors 724a and 724b may be positioned along or aligned with a longitudinal axis/centerline of the prosthetic foot 700. The spring connector 724a, 724b may be spaced apart in the longitudinal direction. In other embodiments, the spring connector 724a, 724b may be positioned at various offset directions in the medial or lateral direction while still being aligned longitudinally, or may be spaced apart both longitudinally and in the medial/lateral direction. FIGS. 20A and 20B show the spring connectors as loop-shaped structures similar to what is shown in FIGS. 1-16. However, the spring connectors may also be linear strands such as the embodiments of FIGS. 17-19.

FIG. 21C shows a prosthetic foot 800 with a base spring 812 and first and second top springs 814, 816. A plurality of spring connectors 824a-c provided as separate, linear spring connectors (e.g., similar to those shown in FIGS. 17-20) positioned in spaced apart longitudinal and medial/lateral directions. The spring connectors 824a-c may include a connecting member 825a-c, respectively. The connecting members 825a-c may include, for example, a knot, a crimped member, or a frayed end such as those described with reference to FIGS. 17-20, or other feature that help secure the springs 812, 814, 816 together.

Although the embodiments of FIGS. 21A-C show the spring connectors connecting all three of the base spring and first and second top springs together, it is possible to use any of these spring connector orientations shown in FIGS. 21A-21C in embodiments where only the first top spring is connected to the base spring (e.g., similar to prosthetic foot 10 described above). Still further, when two or more spring connectors are used, one spring connector may provide a connection only between the base spring and the first top spring, and the second spring connector may provide a connection between all three of the base spring and first and second top springs. Alternatively, one or more spring connectors may be used to secure only the top springs to each other rather than connecting the base spring to one or more top springs.

One aspect of the present disclosure relates to the spring connectors penetrating through one or more of the springs of the prosthetic foot, preferably in the forefoot area of the prosthetic foot. The spring connector may penetrate through one or more of the springs at multiple locations. Alternatively, separate spring connectors may penetrate through one or more of the springs at various locations in the longitudinal as well as the medial/lateral direction. The spring connectors disclosed herein may be used in combination with a bond connection between one or more of the springs of the prosthetic foot. Although the spring connectors may overlap with and/or penetrate through such bond connections, some embodiments provide for the spring connectors to be arranged spaced apart from one or more of the bond connections so as not to penetrate through such bond connections.

The spring connectors described herein may provide additional resistance against unintentional separation of the springs of a prosthetic foot. The spring connectors may reduce the likelihood of failure of one or more connections between any of the springs of the prosthetic foot. In one example, the use of one or more spring connectors in combination with a bond connection between two or more springs of a prosthetic foot may increase the useful life of the prosthetic foot (e.g., determined by a number of gate cycles by X amount [inventors, provide some details about the advantages related to using the stitching]. The use of one or more of the spring connectors disclosed herein without a separate bond connection may also provide certain advantages as compared to using a bond connection alone or using a rigid spring connector alone or in combination with a bond connection.

The spring connectors described herein may be referred to as stitching or stitches. Such spring connectors may comprise various materials, including, for example, manmade materials, natural materials, polymeric materials, metallic materials and alloys. Although some embodiments may include inextensible materials, other embodiments may include materials that are flexible along their length, but only flexible within a limited range (e.g., in a range that is similar to the compression/extension properties of the bond material with which the spring connectors are used to connect the springs to the prosthetic foot).

Referring now to FIG. 22, an example method 900 of manufacturing a prosthetic foot in accordance with the present disclosure is shown as a flow diagram. The method 900 includes, at block 905, providing a base spring, a prosthesis connector, at least a first spring member, and at least a first spring connector. The method 900 also includes, at block 910, connecting the prosthesis connector to a proximal end of the first spring member. Block 915 includes connecting a distal end portion of the spring member and a portion of the base spring with a first spring connection. Block 920 includes forming a first passthrough bore through the first spring member, the base spring and the first spring connection. Block 925 includes positioning the first spring connector in the passthrough bore, the first spring connector providing a secondary connection between the base spring and the first spring member.

Method 900 may also include forming a second passthrough bore through the first spring member, the base spring and the first spring connection, and positioning the first spring connector in the second passthrough bore. The first spring connector may have a loop shape. The method 900 may also include providing a second spring member and arranging the second spring member in parallel with and spaced apart from the first spring member, and connecting distal ends of the first and second spring members to each other with a second spring connection, wherein the first passthrough bore extends through the second spring member and the second spring connection, and the first spring connector provides at least one of a secondary connection between the first and second spring members and a connection between the second spring member and the base spring. The method 900 may include forming third and fourth passthrough bores through the first spring member, the base spring and the spring connection, and positioning a second spring connector in the third and fourth passthrough bores, the second spring connector providing another secondary connection between the base spring and the first spring member. The method 900 may include forming a second passthrough bore through the first spring member, the base spring and the first spring connection, and positioning the second spring connector in the second passthrough bore, the second spring connector providing another secondary connection between the base spring and the first spring member. The method 900 may further include forming a second passthrough bore through the first and second spring members, the base spring and the first and second spring connections, and positioning the first spring connector in the second passthrough bore, the second spring connector having a loop shape.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon."

What is claimed is:

1. A prosthetic foot, comprising:
a base spring comprising a forefoot portion, a mid-section portion, and a posterior end portion;
a top spring assembly, comprising:
a first spring member having a distal end and a proximal end;
a second spring member positioned below a bottom surface of the first spring member, the second spring member being spaced apart from the first spring member along its entire length and having a distal end and a proximal end; and
a first bond connection positioned below a bottom surface of the second spring member and above a top surface of the base spring, the first bond connection positioned at the distal end of the second spring member and at the forefoot portion of the base spring;
a first spring connector extending through a first set of holes formed along the forefoot portion of at least the base spring, the first bond connection, and the second spring member; and
a second spring connector extending through a second set of holes formed along the forefoot portion of at least the base spring, the first bond connection, and the second spring member,
wherein:

the first spring connector and the second spring connector are positioned in a side-by-side arrangement along a transverse direction of the prosthetic foot, the first spring member is positioned on top of the first spring connector and the second spring connector, and the first spring member does not include either the first set of holes or the second set of holes, and the first spring connector and the second spring connector each comprise one of a thread, a string, a strand, a cord, a tow, a roving, a braid, a lashing, and a cable.

2. The prosthetic foot of claim 1, further comprising a second bond connection provided between the distal ends of the first and second spring members.

3. The prosthetic foot of claim 2, wherein the first set of holes and the second set of holes are formed in the second bond connection, the first spring connector and the second spring connector extend through the second bond connection.

4. The prosthetic foot of claim 2, wherein the second bond connection provides a spacing between the distal ends of the first and second spring members.

5. The prosthetic foot of claim 1, wherein the first spring connector and the second spring connector each comprise a flexible material selected from a group consisting of polyester, nylon, poly-paraphenylene terephthalamide, and ultra-high-molecular-weight polyethylene.

6. The prosthetic foot of claim 1, further comprising a spacer positioned between the proximal ends of the first and second spring members.

7. The prosthetic foot of claim 1, wherein the first bond connection is provided by an adhesive.

8. The prosthetic foot of claim 1, further comprising a heel cushion mounted to the base spring at a location spaced forward of the heel end portion of the base spring, the heel cushion arranged to contact a bottom surface of the second spring member during use of the prosthetic foot.

9. The prosthetic foot of claim 1, wherein the base spring further comprises a first slot extending longitudinally through a centerline of the base spring from the forefoot portion through at least a portion of the mid-section portion.

10. The prosthetic foot of claim 9, wherein the base spring further comprises a second slot adjacent to the first slot, wherein the second slot is located in a forward position relative to the top spring assembly.

11. The prosthetic foot of claim 9, wherein the first spring connector and the second spring connector are positioned on different sides of the first slot.

12. The prosthetic foot of claim 9, wherein the first spring member, the second spring member, and the bond connector comprise a slot that aligns with the first slot of the base spring.

13. The prosthetic foot of claim 1, wherein the first bond connection comprises flexible material to allow flexible movement between the base spring and the second spring member.

14. The prosthetic foot of claim 1, wherein the first spring connector forms a first loop through the first set of holes and the second spring connector forms a second loop through the second set of holes.

15. The prosthetic foot of claim 1, wherein the first set of holes and the second set of holes are positioned in the forefoot portion of the base spring.

16. The prosthetic foot of claim 15, wherein the first set of holes and the second set of holes are positioned at a proximal end of the first bond connector.

17. The prosthetic foot of claim 15, wherein the first spring connector and the second spring connector comprises opposite free ends at least partially secured together by a knot, adhesive, melting, or a combination thereof.

18. The prosthetic foot of claim 15, wherein the first spring connector and the second spring connector are inextensible.

19. A prosthetic foot, comprising:

a prosthesis connector configured to connect the prosthetic foot to a lower limb prosthesis;

a base spring comprising a forefoot portion, a mid-section portion, and a posterior end portion;

a first spring member having a distal end and a proximal end;

a second spring member having a distal end and a proximal end;

a first bond connection positioned between a bottom surface of the first spring member and a top surface of the base spring, the first bond connection positioned at the distal end of the first spring member and at the forefoot portion of the base spring;

a first spring connector positioned in a first pass through bore, the first pass through bore extending through the base spring, the first bond connection, and the first spring member; and a second spring connector positioned in a second pass through bore, the second pass through bore extending through the base spring, the first bond connection, and the first spring member, wherein:

the first spring connector and the second spring connector are positioned in a side-by-side arrangement along a transverse direction of the base spring and the first spring member, the first pass through bore and the second pass through bore are positioned in the forefoot portion of the base spring, the second spring member is positioned on top of the first spring connector and the second spring connector, and the second spring member does not include either the first pass through bore or the second pass through bore, and the first spring connector and the second spring connector each comprise one of a thread, a string, a strand, a cord, a tow, a roving, a braid, a lashing, and a cable.

20. The prosthetic foot of claim 19, wherein the first and second spring connectors have a loop shaped construction.

21. The prosthetic foot of claim 19, further comprising: a third pass through bore adjacent to the first pass through bore extending through the base spring, the first bond connection, and the first spring member, wherein the first spring connector comprises a loop shape construction that passes through the third pass through bore; and a fourth pass through bore adjacent to the second pass through bore extending through the base spring, the first bond connection, and the first spring member, wherein the second spring connector comprises a loop shaped construction that passes through the fourth pass through bore.

22. The prosthetic foot of claim 21, further comprising a balance slot extending along a longitudinal centerline of the base spring and the first spring member, wherein the first and third pass through bores are positioned on a first side of the balance slot and the second and fourth pass through bores are positioned on a second side of the balance slot opposite the first side.

\* \* \* \* \*